(12) United States Patent
Forsell

(10) Patent No.: US 9,017,403 B2
(45) Date of Patent: *Apr. 28, 2015

(54) BREAST IMPLANT SYSTEM

(76) Inventor: Peter Forsell, Bouveret (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/384,366

(22) PCT Filed: Jul. 13, 2010

(86) PCT No.: PCT/EP2010/060079
§ 371 (c)(1),
(2), (4) Date: Jan. 17, 2012

(87) PCT Pub. No.: WO2011/006901
PCT Pub. Date: Jan. 20, 2011

(65) Prior Publication Data
US 2012/0116508 A1 May 10, 2012

Related U.S. Application Data

(60) Provisional application No. 61/213,811, filed on Jul. 17, 2009.

(51) Int. Cl.
*A61F 2/12* (2006.01)
(52) U.S. Cl.
CPC ............ *A61F 2/12* (2013.01); *A61F 2250/0003* (2013.01); *A61F 2250/0004* (2013.01)
(58) Field of Classification Search
USPC ......................................................... 623/7–8
See application file for complete search history.

(56) References Cited

U.S. PATENT DOCUMENTS

| 3,683,424 A |   | 8/1972  | Pangman |
|---|---|---|---|
| 4,217,889 A |   | 8/1980  | Radovan et al. |
| 4,507,810 A |   | 4/1985  | Bartholdson |
| 4,531,244 A | * | 7/1985  | Hamas .............................. 623/8 |
| 4,615,704 A |   | 10/1986 | Frisch |
| 4,636,213 A |   | 1/1987  | Pakiam |
| 4,662,357 A |   | 5/1987  | Pierce et al. |

(Continued)

FOREIGN PATENT DOCUMENTS

| EP | 0 357 927 | 3/1990 |
|---|---|---|
| WO | WO 96/40003 | 12/1996 |

(Continued)

OTHER PUBLICATIONS

International Search Report for PCT/EP2010/060078, mailed Sep. 3, 2010.

(Continued)

*Primary Examiner* — Suzette J Gherbi

(57) ABSTRACT

A breast implant system comprises at least one first element (1) and at least one second element (2) for implantation in the patient's body so as to form part of a breast implant (10). The first element is displaceable relative to the second element, when implanted in the patient's breast, so as to change the outer shape of the breast implant. Preferably, the elements are contained in a casing (12, 13) with a flexible outer shape. More preferably, a reservoir (R) comprising a lubricating fluid is connected to the casing so as to allow lubricating fluid to be supplied to, and removed from, the casing, in order to reduce surface friction between adjacent elements, and/or between the casing and the elements, before the shape of the breast implant is changed by relative displacement of the first and second elements.

54 Claims, 17 Drawing Sheets

(56) References Cited

U.S. PATENT DOCUMENTS

| | | | |
|---|---|---|---|
| 4,671,255 A * | 6/1987 | Dubrul et al. | 128/899 |
| 4,731,081 A | 3/1988 | Tiffany et al. | |
| 4,790,848 A | 12/1988 | Cronin | |
| 4,984,585 A | 1/1991 | Austad | |
| 5,146,933 A | 9/1992 | Boyd | |
| 5,236,454 A | 8/1993 | Miller | |
| 5,549,671 A | 8/1996 | Waybright et al. | |
| 5,571,178 A * | 11/1996 | Ledergerber | 623/8 |
| 5,723,006 A * | 3/1998 | Ledergerber | 623/8 |
| 5,779,734 A | 7/1998 | Ledergerber | |
| 5,882,353 A | 3/1999 | Vanbeek et al. | |
| 6,187,043 B1 | 2/2001 | Ledergerber | |
| 6,668,836 B1 | 12/2003 | Greenburg et al. | |
| 6,755,861 B2 | 6/2004 | Nakao | |
| 6,875,233 B1 | 4/2005 | Turner | |
| 7,081,136 B1 | 7/2006 | Becker | |
| 7,575,596 B2 * | 8/2009 | Bowman et al. | 623/7 |
| 8,398,710 B2 | 3/2013 | Forsell | |
| 2001/0010024 A1 | 7/2001 | Ledergerber | |
| 2002/0143396 A1 | 10/2002 | Falcon et al. | |
| 2003/0074084 A1 | 4/2003 | Nakao | |
| 2006/0069403 A1 | 3/2006 | Shalon et al. | |
| 2006/0111791 A1 | 5/2006 | Forsell | |
| 2006/0235482 A1 | 10/2006 | Forsell | |
| 2009/0012372 A1 | 1/2009 | Burnett et al. | |
| 2009/0082864 A1 * | 3/2009 | Chen et al. | 623/8 |
| 2009/0192533 A1 | 7/2009 | Dlugos et al. | |
| 2009/0210056 A1 | 8/2009 | Forsell | |
| 2009/0299473 A1 | 12/2009 | Govrin-Yehudian et al. | |
| 2011/0054606 A1 | 3/2011 | Forsell | |
| 2011/0196422 A1 | 8/2011 | Forsell | |
| 2011/0264213 A1 * | 10/2011 | DeMiranda | 623/8 |
| 2012/0022324 A1 | 1/2012 | Forsell | |
| 2012/0078366 A1 * | 3/2012 | Jones et al. | 623/8 |
| 2012/0116508 A1 | 5/2012 | Forsell | |
| 2012/0116509 A1 * | 5/2012 | Forsell | 623/8 |
| 2012/0123536 A1 * | 5/2012 | Kronowitz | 623/8 |

FOREIGN PATENT DOCUMENTS

| | | |
|---|---|---|
| WO | WO 97/40749 | 11/1997 |
| WO | WO 2006/034273 | 3/2006 |
| WO | WO 2006/079905 | 8/2006 |
| WO | WO 2006/079905 A2 | 8/2006 |
| WO | WO 2007/004213 | 1/2007 |
| WO | WO 2008/053630 | 5/2008 |

OTHER PUBLICATIONS

Written Opinion of the International Searching Authority for PCT/EP2009/000622, mailed Apr. 1, 2009, corresponding to related co-pending U.S. Appl. No. 12/865,306, filed Jul. 29, 2010.
International Search Report issued in corresponding International Application No. PCT/EP2009/000622, mailed Apr. 1, 2009.
Written Opinion of the International Searching Authority for PCT/EP2010/060078, dated Sep. 3, 2010.
International Search Report for PCT/EP2010/060079, mailed Nov. 23, 2010.
Written Opinion for PCT/EP2010/060079, mailed Nov. 23, 2010.
U.S. Appl. No. 12/320,670 (Forsell) filed Jan. 30, 2009.
U.S. Appl. No. 12/865,306 (Forsell) filed Oct. 21, 2010.
U.S. Appl. No. 13/384,471 (Forsell) filed Jan. 17, 2012.

* cited by examiner

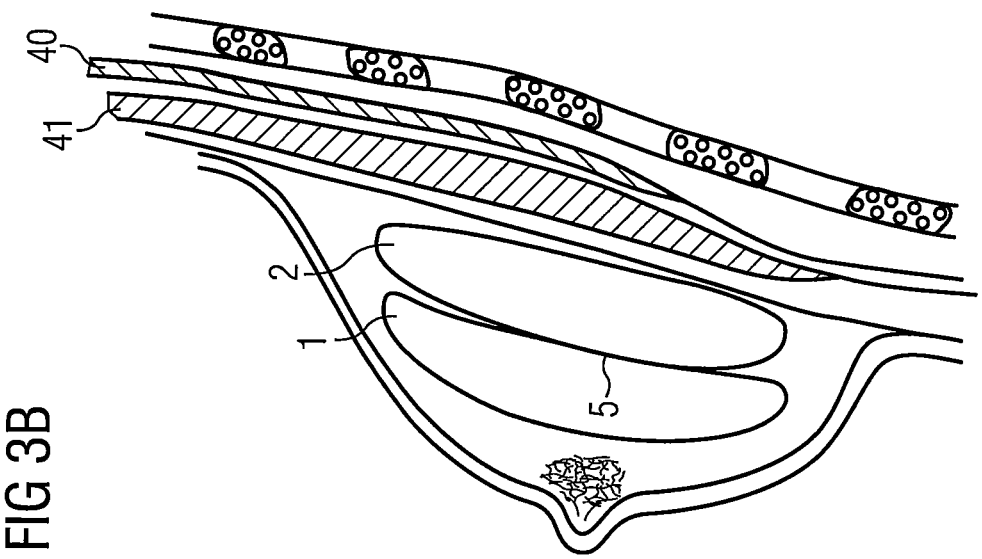
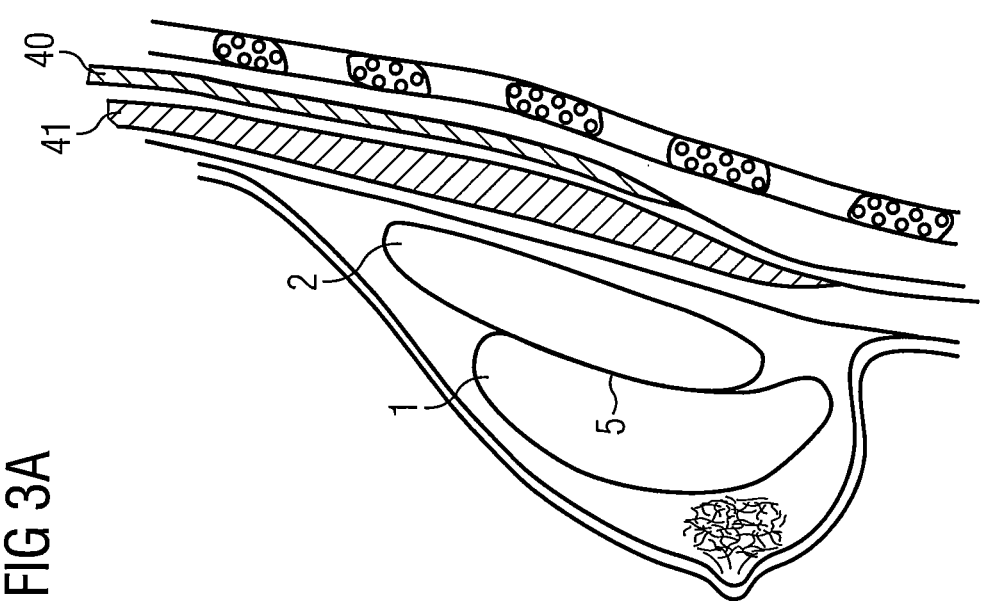

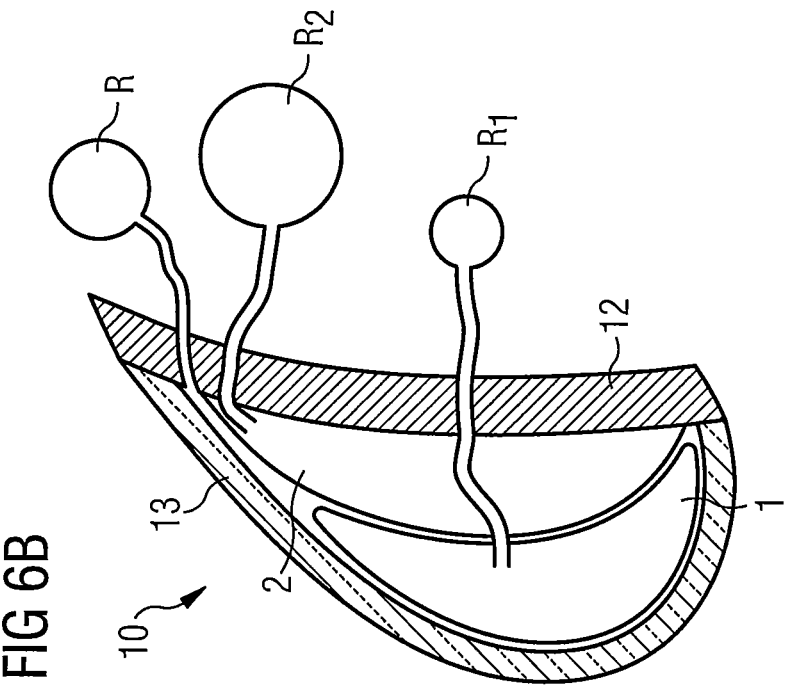
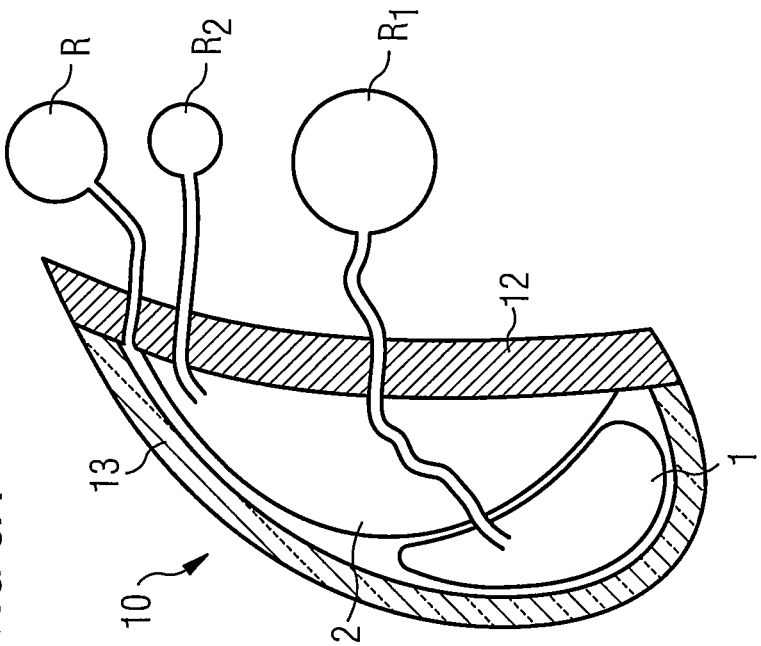

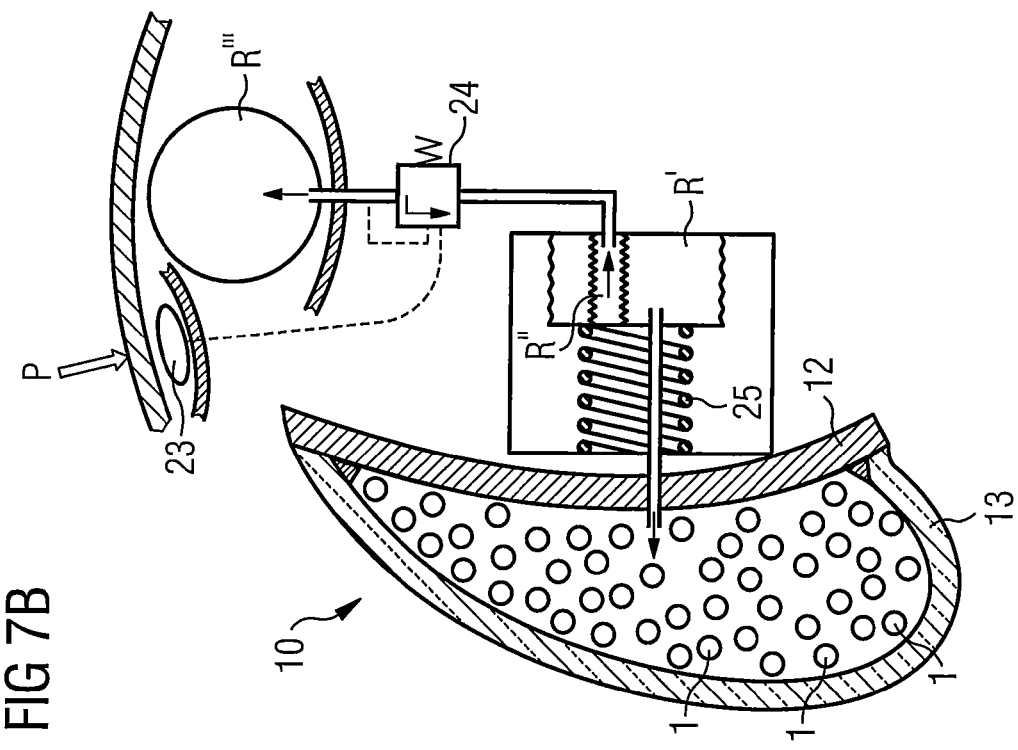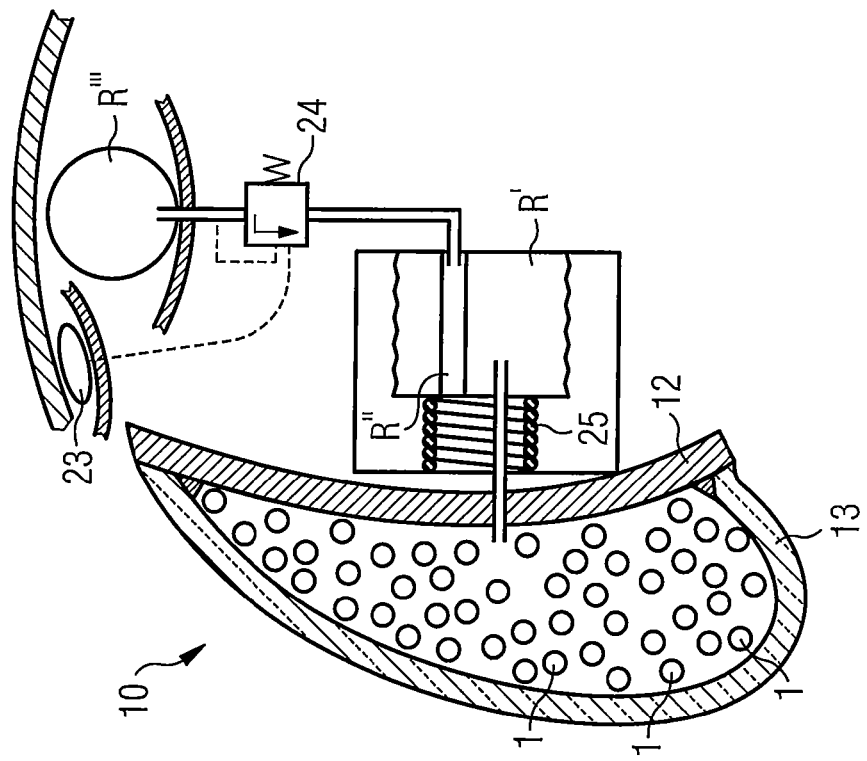

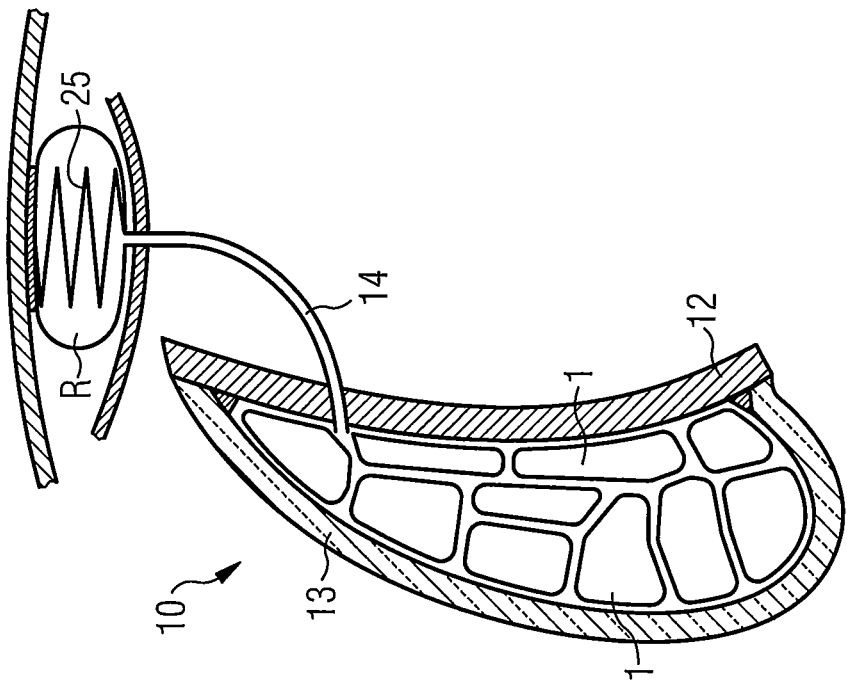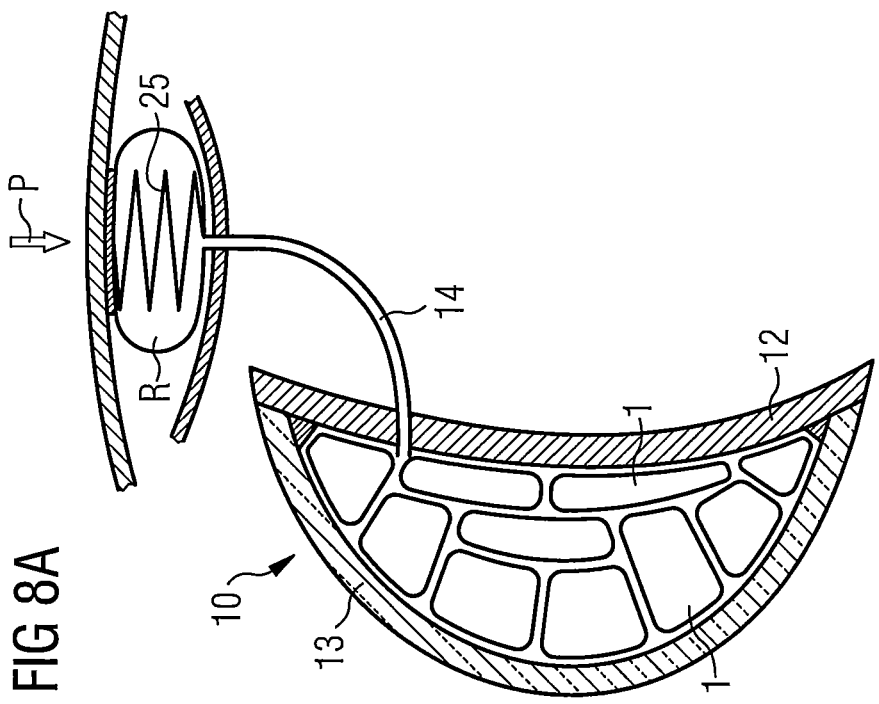

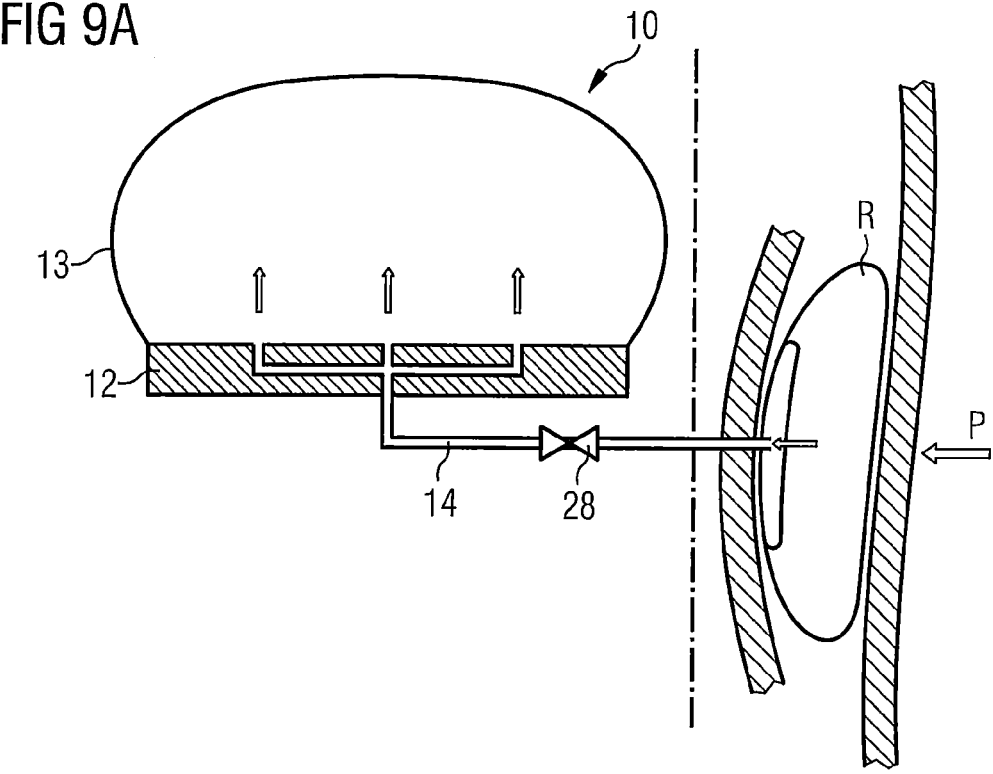
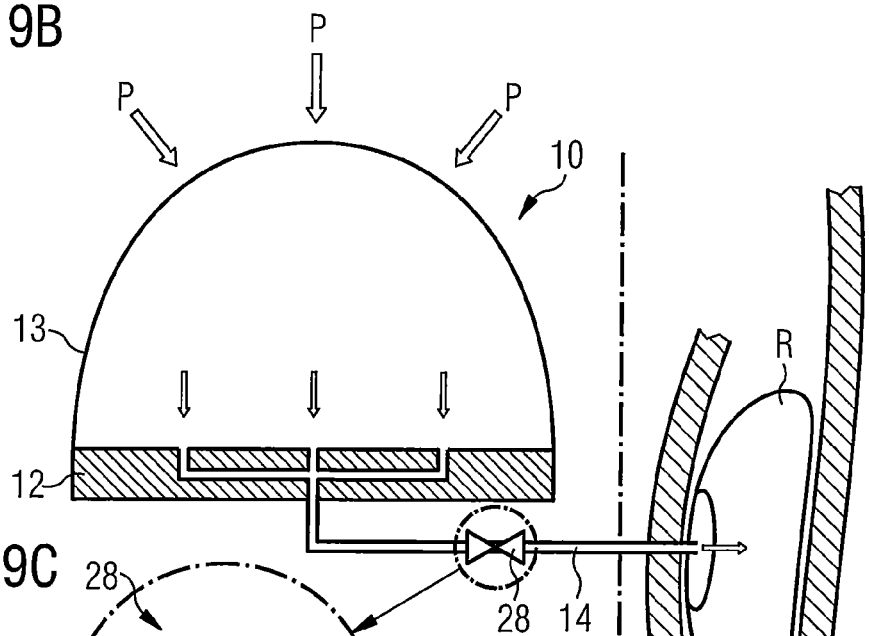
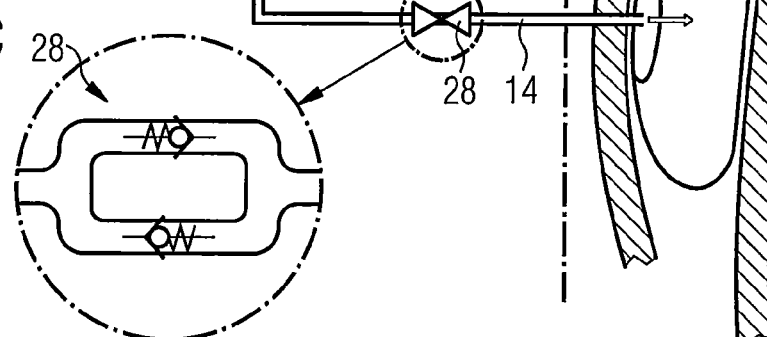

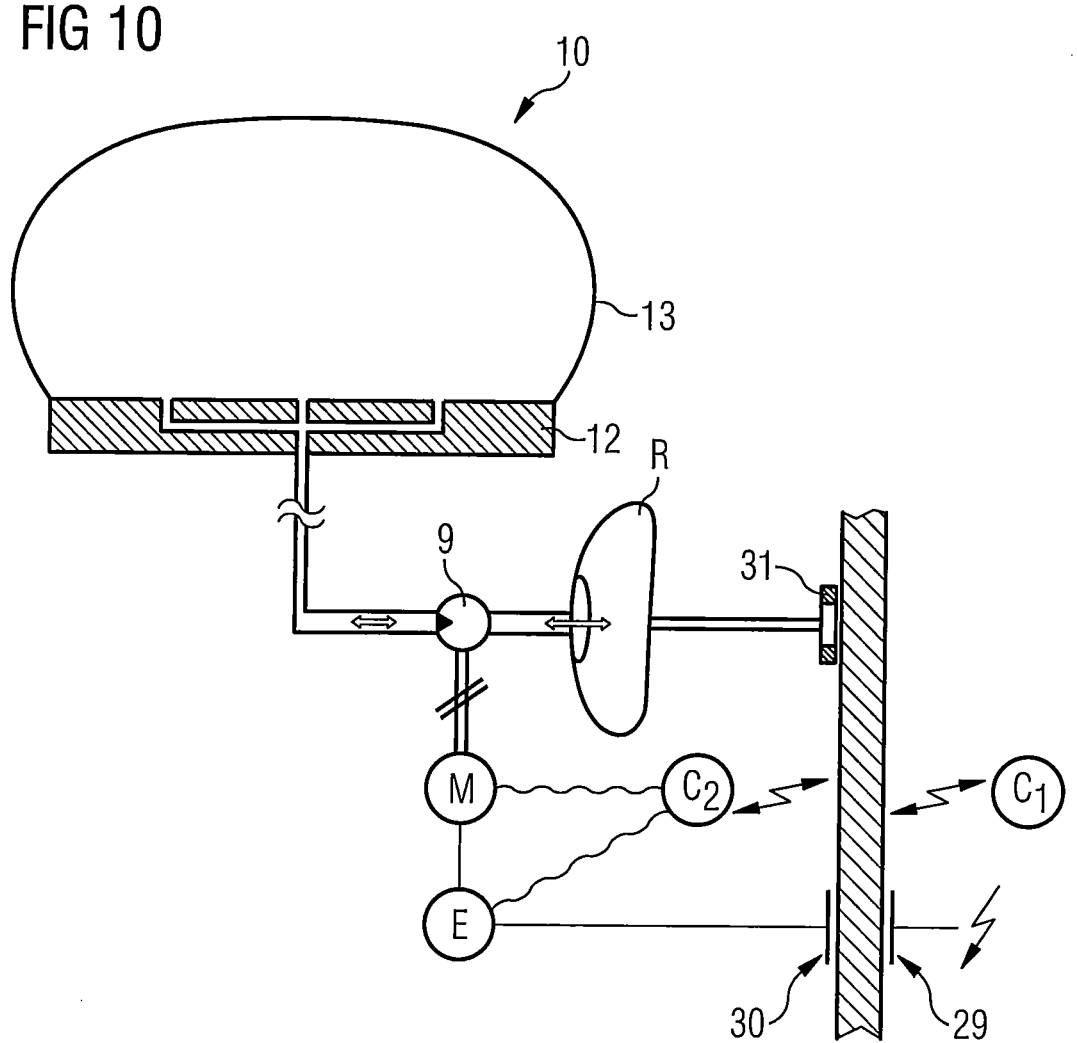

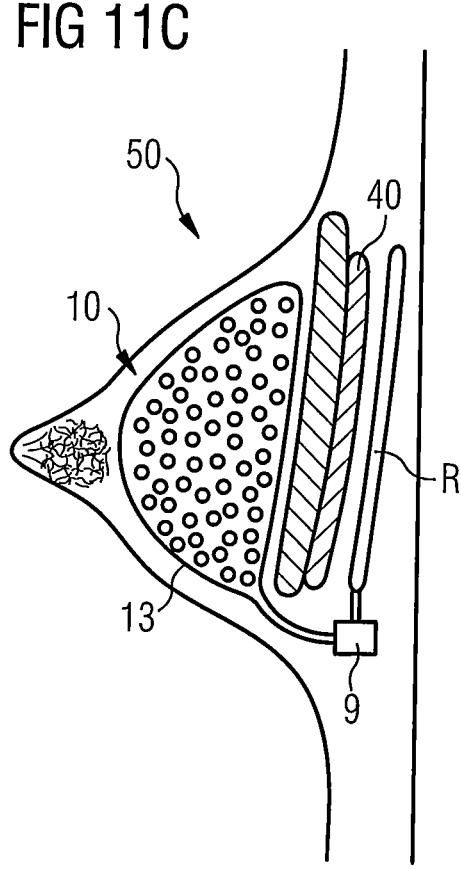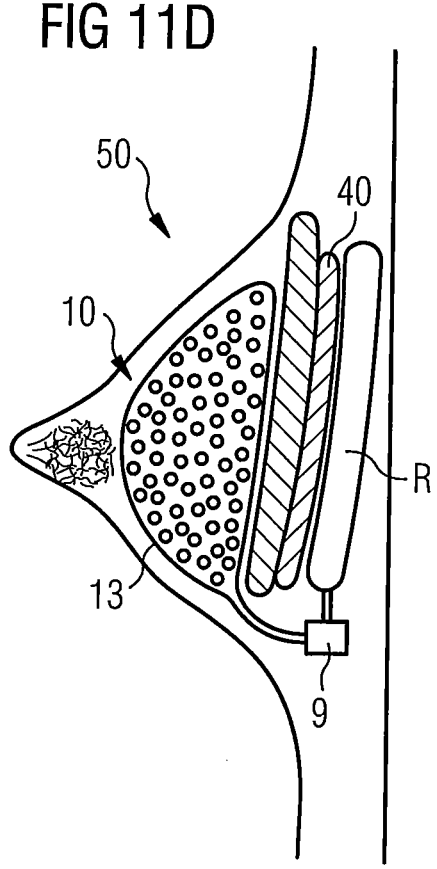

BREAST IMPLANT SYSTEM

This application is the U.S. national phase of International Application No. PCT/EP2010/060079, filed 13 Jul. 2010, which designated the U.S. and claims the benefit of U.S. Provisional No. 61/213,811, filed 17 Jul. 2009, the entire contents of each of which are hereby incorporated by reference.

BACKGROUND OF THE INVENTION

The present invention relates to a breast implant system that allows the shape of a breast implant to be varied after its implantation in the patient's body.

Breast implants are typically used to replace a natural breast that has been removed, e.g. due to cancer, or to increase the size of a natural breast, when the natural size is considered unsatisfactory. In general, people who desire to change the overall size and shape of the breast implants after implantation have to undergo major surgery. It would be desirable for the patient to adjust the size and shape of the breast implant easily, depending on current needs. For instance, as time goes by the patient might no longer be happy with the size or shape of the artificial breast. Alternatively, the patient might want to change the shape or size only temporarily. For instance, one might wish to reduce the height of the breast implant during sports activities or one might wish to enlarge the height for a particular event, such as a formal evening affair.

U.S. Pat. No. 6,875,233 B1 discloses a breast implant that allows the overall size and shape thereof to be changed once it has been surgically implanted. This breast implant includes an exterior shell and an inner bladder. The exterior shell is typically a bellows having a plurality of pleats, so that the outer size of the implant is variable. As the bladder is filled, the exterior shell expands in a manner that creates a lifting effect and a ballooning effect. A valve connected to both the exterior shell and the inner bladder can be used to fill the bladder external to the patient without the need for further surgery after the implant has been implanted in the patient. The bladder may be filled with a liquid, a gas, or a solid, and such filler can be added and removed through the valve as needed. The valve either remains external, so that it can be used without any further surgery, or it can be located under the patient's skin, in which case minor surgery must be performed to access the valve.

The options for changing the shape of this prior art breast implant are limited. In addition, it is inconvenient for the patient that the valve for accessing the inner bladder of the breast implant permanently penetrates the patient's skin or, where it is implanted subcutaneously, requires minor surgery to be accessed.

US 2003/0074084 A1 discloses a breast implant with a plurality of chambers. The chambers are differently pressurized in order to control the shape of the breast implant upon inflation thereof. Each chamber may be provided with a pair of conduits for alternatively delivering fluid to and removing fluid from the chambers. Terminal connectors of such conduits can be easily located by medical practitioners for delivery of fluid to or removal of fluid from a desired chamber either manually or assisted by machinery. Alternatively, fluid can be supplied or removed by inserting a hollow needle directly into the chambers of the breast implants.

While the options of changing the shape of this prior art breast implant are improved over the breast implant disclosed in U.S. Pat. No. 6,875,233 B1, a medical practitioner is still needed to achieve different sizes and shapes of the breast implant after its implantation.

In a simpler embodiment described in US 2003/0074084 A1, one-way valves are each disposed between two adjacent chambers for enabling a transfer of fluid from a first to a second of the adjacent chambers, upon application of an external compressive force to the first chamber. This way, the valves enable reshaping of the breast implant merely through manipulation. It is even suggested to automatically open and close the valves by wireless remote control.

PCT/EP2009/000622 also relates to a breast implant system comprising a plurality of chambers which are interconnected when implanted, such that fluid can be exchanged between them, so as to change their respective fluid content. Various embodiments are disclosed for: changing the shape but not the volume; for changing the shape, and also the volume without a change of the breast implant's mass (this being achieved by causing a gas-filled chamber to be compressed when liquid is exchanged between chambers of the breast implant); and for changing the shape, and also the volume of the breast implant involving a change of the breast implant's mass. It is further described that fluid exchange between the chambers can be achieved by manually compressing the one or the other fluid chamber, similar to the afore-mentioned US 2003/0074084 A1. However, preferred embodiments include a fluid reservoir implanted remotely from the breast implant in the patient's abdominal cavity, or inside the patient's chest area, such as outside the thorax under the minor pectoralis muscle, or between the major and the minor pectoralis muscles. A pump may be provided for pumping the fluid between the chambers of the breast implant, and/or between one or more chambers and the remotely implanted reservoir. The pump may be manually driven, for which purpose it is advantageously implanted subcutaneously. Alternatively, the pump may be driven by a motor, which may likewise be implanted. Pump and/or motor may be driven by energy wirelessly transmitted from outside the patient's body. A control unit for controlling the entire process, in particular wirelessly, may be further provided. The breast implant may further have a rigid back plate, to which at least one chamber is fixedly connected, to provide stiffness, giving the breast implant a basic contour which is maintained throughout any shape changes of the breast implant. Furthermore, in order to improve the overall appearance of the breast implant, the part of the breast implant's outer wall facing away from the patient's chest may comprise a compartment filled with a soft material, such as silicone.

Thus, the breast implant system disclosed in PCT/EP2009/000622 offers a great variety of options for changing the shape and the size of a breast implant after its implantation. The changes can be easily carried out and controlled by the patient without any medical practitioner being involved.

U.S. Pat. No. 5,356,429 suggests to place a liner material in a body pocket in which the breast implant is to be placed. The liner material may be formed of a single sheet or a number of sheets of elastomeric material and is smooth on one side and textured on the other side. The textured side will allow growth thereonto of tissue against which it is positioned, whereas the smooth side will not adhere or allow growth thereonto of tissue against which it is positioned. This way, since one side of the liner does not adhere to the body pocket wall, the breast implant is allowed to flow or move within the pocket easily. In a specific embodiment two of those liners are provided facing each other with their smooth sides allowing the breast implant to readily slight between them.

SUMMARY OF THE INVENTION

It is an object of the present invention to provide a breast implant, or, more specifically, a breast implant system that allows for an easy manipulation of the breast implant when varying the shape thereof.

A breast implant system according to the present invention comprises at least one first element and at least one second element to be implanted in the patient's body to form part of a breast implant. The first element and the second element (or elements) each comprise an outer wall defining a volume which is filled or fillable with a filling material, i.e. they are provided as filled hollow bodies. Alternatively, either or both of the first and second elements may be provided in granular form. The first element is displaceable relative to the second element. That is, the first element can be moved, when implanted in the patient's breast, between different spots within the breast to change the outer shape of the breast. Thus, by simple manipulation from outside the patient's breast, the two or more elements can be rearranged within the breast. For instance, the two elements may be pad-like or cushion-like. When one element is positioned at least partly below or beside the respective other element, the breast will have a relatively flat shape. By manually manipulating the breast from outside, the two elements may be relocated within the patient's breast, so that they lie on top of each other in the most extreme situation, in which case the breast will assume a relatively steep shape.

While in a most simple configuration the two (or three or even more) elements are freely moveable relative to each other, it is advantageous to limit their movability within certain boundaries. Therefore, at least one of the elements may be fixedly mounted. For instance, it is described in WO 2007/004213 A2 how an implant may be fixed to the substantially horizontal rib bones by means of straps having anchoring ends provided with bone anchoring elements. By means of those straps, one or more of the elements can be mounted to remain substantially stationary, whereas one or more of the remaining elements may be freely displaceable relative to the fixedly mounted element or elements. This configuration contributes to the breast maintaining a certain basic shape that can be changed in a limited way by relocating the remaining element or elements.

Alternatively, or, preferably, in addition to the stationary mounting of one or more elements, it is advantageous to interconnect the first and second elements, or at least some of them, to limit their relative displaceability. This constructional aspect further contributes to the breast maintaining a basic shape that can be modified manually from outside the patient's breast within certain limits.

It is even more advantageous when the first and second elements are mounted to be movable only between predetermined spots. This will minimize the efforts that have to be taken during the reshaping step, and will simplify the overall procedure. For instance, it will be easy for the user to change the shape of the breast implant from one extreme to another extreme, e.g. from flat to high, because the extreme positions are defined by the limits of movement of the elements. For instance, the elements may be mounted to each other by straps or may be otherwise interconnected, such as gluing together a section of the flexible walls of the pad-like or cushion-like elements. Alternatively or in addition, they may be hinged to the bone structure, as mentioned above.

However, most preferably the elements are contained in a casing in order to isolate them from living tissue. Living tissue will soon overgrow the elements if not contained in a casing and, thus, hinder manipulation and relocation of the elements within the breast. Within such casing, at least a first one of the elements would be movable between different spots.

At least a second one of the elements may form part of a wall of the casing so that it assumes a relatively fixed position within the breast. Only the first element would have to be moved between different spots within the casing by manipulation from outside the patient's breast. Again, such freely movable element may be displaced, e.g., from a position below or beside the fixedly mounted element, to a position on top thereof, so as to reshape the breast from relatively flat to relatively high. The casing itself has a flexible and preferably also stretchable wall, i.e. an elastic wall, to follow any shape changes caused by an internal relocation of the elements.

The flexibility or elasticity of the casing's outer wall is also important in respect of fibrosis covering said outer wall, when the breast implant is implanted in the body. The shape of the casing must be sufficiently flexible to allow lengthening of the functional length thereof without interfering with the fibrosis. For instance, the casing's outer wall may have at least one wrinkle or cease, similar to that of a bellows, to allow lengthening of the outer wall without lengthening fibrosis covering the outer wall when implanted.

The second element may form part of the wall of the casing, or more preferably, part of a rigid back plate of the breast implant. It is particularly advantageous to fixedly mount the second element within the casing, when the first and second elements are somehow interconnected in a manner that limits their relative movement. By mounting the second element fixedly to the casing, predetermined shapes of the breast implant are easy to obtain, because only the first element needs to be displaced, and the displacement can only occur within a predetermined range, due to the first element being connected to the fixedly mounted second element.

According to another embodiment, either, or both, of the first and second elements are mounted within the casing to be movable only between predetermined spots. Thus, the respective element is not fixedly mounted within the casing, but there is a range of spots between which it can be moved. This allows a general structure to be maintained, while permitting certain changes to be made within such structure.

It is even possible to fixedly mount the second element to a wall of the casing, and to mount the first element to be movable within the casing only between predetermined spots. For instance, the first element may be somehow connected to the second element, or may be connected somehow to a wall of the casing, or both. With this arrangement, it is possible to provide a structure in which one or more first element (or elements) is movable from a spot located at least partly beside the second element (which can likewise be said to be a spot above or below the second element, depending upon the perspective), to a spot on top of the second element, so as to change the outer shape of the breast implant, from relatively flat to relatively high.

It should be clear from the above that there are many possibilities of providing and arranging the first and second elements. This includes in particular that two, three, or even more of at least one of the first and second elements may be present.

Alternatively, all of the elements may be moveable within the casing between different spots. In particular, where the elements are not pad-like or cushion-like, but are small and present in an amount of ten or more, hundred or more, or even thousands, it is not necessary to limit their displaceability within the casing.

The actual purpose is in each case to change the outer shape of the breast implant post-operatively, and, in particular, non-invasively.

As mentioned before, the breast implant preferably has a rigid back wall arranged to being placed adjacent the patient's thorax. The back wall provides stiffness and gives the breast implant a basic contour that is maintained throughout any shape changes of the breast implant. The rigid back wall advantageously forms part of the casing. Again, the casing, i.e. preferably the rigid back wall thereof, may be mounted to the patient's bone structure in the manner described before.

In addition to or independent from any rigid back wall, the casing may have a structure comprising at least one compartment filled with a soft material, such as a foam or silicone. This gives the breast implant the look and feel of a natural breast, and can also serve to level out any unevenness caused by different fillings, and/or different pressures, in the elements contained in the breast implant's casing, or caused by an uneven distribution of the elements within the casing.

According to a particularly preferred embodiment, there is further provided a reservoir that comprises a lubricating fluid. The reservoir is connected to the casing to allow the lubricating fluid to be supplied to, and removed from, the interior of the casing. Surface friction between an outer surface of an element contained in the casing, and an adjacent surface of a different element contained in the casing, and/or of the casing itself, and/or of a different component of the breast implant, such as the rigid back plate, can be reduced by supplying lubricating fluid from the reservoir into the casing.

Thus, when one wishes to change the shape of the breast implant, lubricating fluid is first supplied from the reservoir to the casing, so that it can flow between contacting surfaces, thereby reducing surface friction. Next, the shape of the breast implant is changed in any desired manner, e.g., by manually rearranging the elements contained in the casing from outside the breast implant. It should be noted that—although preferred—the invention is not limited to fully implanted breast implant systems, i.e., components thereof may be provided outside the patient's body, such as the lubricating fluid reservoir and the like. Once the shape of the breast implant has been changed by changing the position of one or more elements contained in the casing, the lubricating fluid can be removed from the casing, so that surface friction of the outer surface of the element or elements will increase. The increased surface friction offers the important advantage that the shape of the breast implant obtained by the manipulation of the element or elements within the casing will substantially be maintained over a long period of time. This is particularly important in embodiments where the element or elements are not fixedly connected to a supporting structure, but are, e.g., freely movable within the casing.

Generally, the lubricating fluid may be a liquid or a gas. Where the lubricating fluid is a gas, the casing can be set under gas pressure to inflate the casing, and thereby facilitate manipulation of the element or elements contained in the casing. However, because it is typically dangerous to handle gas within the human body, the lubricating fluid used in connection with the present invention is preferably a liquid or a gel, in particular an isotonic liquid or gel. The use of an isotonic liquid will not cause any harm to the patient in case of any leakage.

The breast implant system of the present invention is preferably a fully implantable system (except possibly for a wireless remote control or wireless energy transfer from outside the patient to the implanted system), with no need for medical practitioners to intervene, in particular without any need for surgery, when the shape of the breast implant is altered. As such, it is preferred to implant the lubricating fluid reservoir within the patient's body along with the breast implant. Because implantation of the breast implant requires surgery in the patient's chest area, the lubrication fluid reservoir may advantageously also be implanted in this area and, more specifically, outside the thorax just like the breast implant. In order not to negatively influence the outer shape of the breast implant, it is preferred that the reservoir is adapted for implantation below the minor pectoralis muscle, or between the major and the minor pectoralis muscles.

However, in order to prevent the lubricating fluid reservoir from having any influence on the outer shape of the breast implant, it may be advantageous to adapt the reservoir so that it can be implanted within the patient's body, remotely from the breast implant, in which case at least one conduit will have to be provided between the remotely implantable reservoir and the casing, in order to allow for fluid exchange between them.

Implanting the lubricating fluid reservoir remotely from the breast implant may also be advantageous for reasons other than the visual appearance of the breast implant.

For instance, the lubricating fluid reservoir may be adapted to be implanted in the armpit, or underneath the patient's arm, where it is hidden but can easily be accessed, such as by the patient manually compressing the reservoir, and, thus, urging lubricating fluid to flow into the casing.

Alternatively, the lubricating fluid reservoir may be adapted for implantation in the patient's abdominal cavity, because the abdominal cavity generally offers more space for implantation, which is particularly advantageous if further components such as a pump and/or a motor and the like are to be implanted along with the reservoir.

It is even possible to implant only a part of the reservoir remotely from the breast implant, while another part is implanted as part of the breast implant, or next to the breast implant. For instance, where a servo system is used to exchange fluid between the reservoir and the casing, as will be described in more detail below, a first part of the reservoir may be implanted, e.g., in the armpit, or underneath the patient's arm, or in the patient's abdominal cavity, in such a way that it is easily accessible by the patient, in particular subcutaneously, and a more voluminous part of the reservoir may be adapted for implantation somewhere else in the patient's body, e.g., next to the breast implant.

As mentioned before, subcutaneous implantation of at least a part of the reservoir can be made, such that manually compressing the subcutaneously implanted part causes fluid to flow from the reservoir into the casing. Advantageously, there is at least one valve provided between the reservoir and the casing, restricting flow in the one and/or in the other direction. For instance, a one-way or two-way valve may be provided to prevent lubricating fluid from flowing back to the reservoir while the size and/or shape of the reservoir is being manipulated. Once a desired size/shape has been achieved, the user may compress the breast implant using both hands, thereby increasing the internal pressure in the casing to a value at which the valve opens, and the lubricating fluid will then flow back into the reservoir. Because only a small amount of lubricating fluid is needed to achieve the friction reducing effect, this procedure will not substantially affect the size/shape of the breast implant. Preferably, the valve is a two-way valve, which opens towards the casing when the (manual) pressure imparted on the reservoir exceeds a predetermined pressure, and opens towards the reservoir when a pressure applied on the casing from outside the breast implant exceeds a predetermined pressure.

In a preferred embodiment, the casing includes hundreds of small elements, and these elements may be granular or spherical, in particular, balls. Preferably, these elements should adhere together in the absence of the lubricating fluid. For instance, the elements may be formed as balls not completely filled, so that they have a slack outer surface. The contacting surfaces of adjacent balls is, thus, relatively large, so that the surface friction resisting relative movement between adjacent balls is likewise relatively large. In the absence of lubricating fluid, the mutual positions of the elements within the casing is unlikely to change substantially over time, whereas the mutual positions of the elements can be easily changed in the presence of the lubricating fluid, e.g., by manual manipulation from outside the breast implant.

It is even within the scope of the present invention that more than one casing is provided in the breast implant. In particular, one or more casings, into which lubricating fluid can be supplied, may be contained within a larger casing, into which the lubricating fluid can likewise be supplied. Thus, the internal casing or casings may constitute "elements" within the larger casing. This way, it is possible to manipulate the elements within the internal casings, which may contain hundreds of small elements as described above, and to manipulate the internal casings within the larger casing, e.g., by rearranging their mutual position within the larger casing.

According to another preferred embodiment of the invention, the element or elements within the casing may have the form of a cushion or pad, as briefly mentioned before, similar to those typically used for increasing the female breast for aesthetic purposes. Such cushions or pads are filled with a material, and have a flexible outer wall, the wall forming the outer surface of the elements. For the reasons already set out before, the flexible outer wall of the cushions or pads are preferably slack to increase the contacting surface area, and, thus, increase surface friction with other cushions or pads in the absence of the lubricating fluid.

The filling material of the pad or cushion may be granular but preferably is a soft material, in particular a fluid. As such, the filling material may comprise gas, liquid, gel, foam or any other flowable material, or a combination of the aforementioned materials. Most advantageously, the filling material is a silicone liquid or a silicone gel, as the consistency thereof comes closest to that of a natural breast.

So far it has been described how the shape of a breast can be changed by relocating, within the patient's breast, one or more of the elements of the breast implant system. The variability of changing the breast implant's shape can be further improved by inter-exchanging content between two or more elements. Of course, these elements need to be interconnected somehow to enable the content exchange. More specifically, such content exchange is preferably such that, by simply manually compressing the one or the other element, fluid is urged to flow from the one element into the other element. For instance, two adjacent elements may be interconnected, e.g., glued together, in a certain area and there may be integrated in such area at least one pressure relief valve which opens at a predetermined pressure. This way, the overall structure can be held relatively simple. More advantageously, the pressure relief valve is a two-way pressure relief valve that opens in the one direction, or the other direction, depending on the side where the predetermined pressure is applied.

Instead of inter-exchanging fluid directly between the first and second elements, an intermediate reservoir may be interposed between the two elements, such that fluid can be exchanged between the intermediate reservoir and the first and second elements, so as to change their respective content. In other words, fluid squeezed out of one element into the intermediate reservoir will cause an equivalent amount of fluid to be urged from the intermediate reservoir into the respective other element. The intermediate reservoir may be arranged, e.g., in a rigid back plate of the breast implant described before.

So far, embodiments have been described wherein the shape of the breast can be changed, e.g., from flat to high, but the size, i.e., the volume of the breast implant, remains constant. According to an even further preferred embodiment, however, the volume of the breast implant can also be changed. For this purpose, at least one reservoir different from the lubricating fluid reservoir is provided in fluid connection with at least one element contained in the casing, such that fluid can be exchanged between this (further) reservoir and the respective element. The further reservoir may be adapted for implantation below the minor pectoralis muscle, or between the major and the minor pectoralis muscles, similar to the lubricating fluid reservoir. It may be placed even more remotely from the breast implant in which case, again, a conduit will have to be provided for the fluid exchange. In addition, a servo system may be added to facilitate the fluid exchange between the further reservoir and the respective element.

In this context, the term "element" may include a chamber having a flexible outer wall and being filled with a fluid, in particular a liquid, and being specifically adapted for supplying fluid to and removing fluid from such chamber in order to ultimately change the size and/or shape of the overall breast implant. The term "element", in this case, may likewise cover a plurality of permanently interconnected chambers. However, where the element or elements have a constant volume, i.e., not being adapted for exchanging fluid content, the content of the elements need not necessarily be a fluid but may likewise be granular. It is not even necessary in such case that the elements have a flexible outer wall. For instance, a great number of small elements, such as 100 or more, may be contained in the casing of the breast implant system, as already mentioned before. These small elements may or may not be entirely stiff. If these elements are contained in a casing of the breast implant according to the previously described preferred embodiment, their purpose is to fill the casing and impart on the casing a particular outer shape which, in turn, defines the outer shape of the breast implant. Thus, by changing the volume of the one or more elements within the casing, and/or by rearranging the element or elements within the casing, the shape and/or size of the breast implant will be affected accordingly.

As previously mentioned, the use of a servo system may facilitate the exchange of fluid between the lubricating fluid reservoir and the casing (and likewise between a "further" reservoir and one or more of the elements contained in the casing). A servo system, in the sense of the present invention, is to be understood as a system in which an amount of fluid is displaced between sub-chambers of the lubricating fluid reservoir, which amount is different to the amount of fluid exchanged between the lubricating fluid reservoir and the casing (or the "further" reservoir and one or more of the elements contained in the casing).

There are various alternative ways of realizing such servo system in the breast implant system of the present invention. In this context, it is preferable to provide a spring element to urge the lubricating fluid reservoir, or at least one of the sub-chambers thereof, into a state of minimum or maximum volume, i.e., into a normally small or a normally large state. Energy, such as a manual compressing force on a subcutaneously implanted sub-chamber, is then only needed to exchange fluid between the casing and the reservoir in one direction, whereas the necessary force required to exchange the fluid in the opposite direction is provided by the spring force. In the same manner, fluid can be exchanged between a further reservoir and one or more elements contained in the casing, in order to change the size and/or shape of the breast implant.

The servo system can be designed as a reverse servo system, to the extent that only a small amount of fluid needs to be exchanged between the sub-chambers of the reservoir in order to achieve a relatively large amount of fluid exchange between the reservoir and the casing. This means that a relatively large force, but small stroke, is needed to achieve the relatively large amount of fluid exchange between the reservoir and the casing. This is particularly convenient where one of the sub-chambers of the reservoir is provided for subcutaneous implantation to be manually compressible by the patient from outside the patient's body. Thus, the subcutaneously arranged compressible sub-chamber may have a relatively small volume, and will therefore not adversely affect the patient's visual appearance, however, with the negative side effect that the patient will have to apply a relatively large force to the relatively small subcutaneous sub-chamber in order to achieve the desired, relatively large fluid exchange. Such sub-chamber can be placed advantageously under the patient's arm.

With time, it may become necessary to add lubricating fluid to the reservoir, or to add to a further reservoir fluid used for inflating and deflating one or more elements contained in the casing. In particular, when gas is contained in one or another reservoir, it is possible that part of the gas will escape over time due to leakage. Therefore, in order to maintain a desired balance in the reservoir or reservoirs, the breast implant system, according to a preferred embodiment, includes at least one injection port for implantation under the patient's skin, so as to allow fluid to be added to, or removed from, any reservoir by injection from outside the patient's body. Thus, the injection port is primarily provided for calibrating purposes. Preferably, the system is adapted to maintain shape and size of the breast implant while fluid is added to or removed from the reservoir via said injection port. Then, after fluid has been added or withdrawn from said injection port, the breast implant is adapted to change shape or size to a larger or lesser extent in a calibration procedure.

The injection port or ports can further be used to adjust the pressure in the breast implant system. For instance, when a patient has achieved a particular distribution of fluid among fluid-filled elements contained in the casing, it is convenient for the patient to release any excess pressure from the system by selectively removing fluid from the system through the injection port or ports.

A pump may be provided in the breast implant system for exchanging lubricating fluid between the reservoir and the casing. The same pump, or a different pump, may likewise be used for pumping fluid between fluid-filled elements contained in the casing, or for pumping fluid into and out of one or more fluid-filled elements contained in the casing. The further reservoir may alternatively be connected to the pump, so as to allow for fluid exchange between fluid-filled elements in the casing by pumping fluid with said pump, from a first element into the further reservoir, and from the further reservoir into the second element, and vice versa.

The pump or pumps may be adapted for implantation under the patient's skin, to be manually operable through the skin. In this case, a purely hydraulic or purely pneumatic pump may be used.

However, where the pump is not manually operable, the breast implant system may comprise at least one motor for automatically driving the pump. In this case, the pump may be of the hydraulic, pneumatic, or mechanical type. In addition, a manually operable switch for activating the motor may be arranged subcutaneously for operation by the patient from outside the patient's body. The motor itself may be arranged to be driven by electric or electromagnetic energy, by an electric or magnetic pulsating field, or by ultrasonic energy.

The breast implant system may further comprise an energy source for supplying the energy, directly or indirectly, to at least one energy consuming part of the system, in particular, to the aforementioned motor for driving the pump. Such energy source may include energy storage means, such as a battery or an accumulator, in particular one or more of a rechargeable battery and a capacitor.

The energy source, when provided outside the patient's body, preferably comprises a wireless energy transmitter for wirelessly transmitting energy from outside the patient's body, directly or indirectly, to the energy consuming part, or to an implanted energy storage means.

The breast implant system preferably further comprises an implantable energy-transforming device for transforming wirelessly transmitted energy into electric energy. The electric energy is stored in the energy storage means, and/or is used to drive the energy consuming part, such as the motor and the pump, as the energy-transforming device transforms the wireless energy into the electric energy. Alternatively, the energy consuming part may be adapted to directly transform the wirelessly transmitted energy into kinetic energy.

It is further preferred to provide the breast implant system with a control unit to directly or indirectly control one or more elements of the breast implant system, in particular the pump and the motor. For instance, the control unit may be primarily adapted to control the exchange of lubricating fluid between the reservoir and the casing, and/or to control fluid flow into, out of, or between one or more elements contained in the casing. Preferably, such controlling action is carried out non-invasively from outside the patient's body, such as by wireless remote control. In this case, a part of the control unit is implanted in the patient's body, whereas another part is not implanted. In particular, in the case where the control unit is completely implanted in the patient's body, a manually operable switch for activating the control unit may be arranged subcutaneously to be operable from outside the patient's body.

Where one part of the control unit is provided outside the patient's body, and the other part is implanted in the patient's body, the external part of the control unit may be used to program the implanted part of the control unit, preferably wirelessly. In addition, the implantable part of the control unit may be adapted to transmit feedback signals to the external part of the control unit. Such signals may relate to: functional and/or physical parameters of the system, and/or patient; and/or may relate to the energy stored in the energy storage means; and/or to an energy balance of the system.

The invention will now be described in more detail in context with some preferred embodiments of the invention as shown in the accompanying drawings.

BRIEF DESCRIPTION OF THE DRAWINGS

FIGS. 3A-3D show a breast implant system according to a third embodiment of the present invention, FIGS. 6A-6B show a breast implant system according to a sixth embodiment of the present invention, FIGS. 7A-7D show a breast implant system according to a seventh embodiment of the present invention, FIGS. 8A-8B show a breast implant system according to an eighth embodiment of the present invention, FIGS. 9A-9C shows a breast implant system according to a ninth embodiment of the present invention, FIG. 10 show a breast implant system according to a tenth embodiment of the present invention, FIGS. 11A-11D shows a breast implant system according to an eleventh embodiment of the present invention.

DETAILED DESCRIPTION OF PREFERRED EMBODIMENTS

Figure 1A:
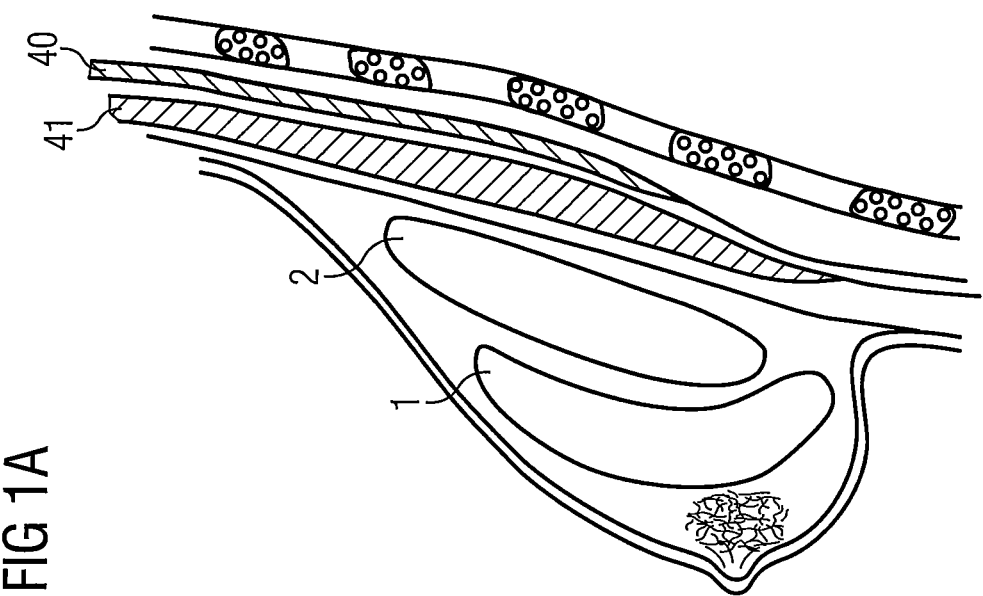
FIGS. 1A-1B show a breast implant system according to a first embodiment of the present invention.

FIG. 1A shows, very schematically, a vertical cross-sectional view of a breast implant system according to a first embodiment. The breast implant system comprises a first element 1, and a second element 2, to be implanted in the breast area of a patient. The first and second elements, 1 and 2, are in the shape of cushions, and may be filled with a fluid, gel, or fine granular material. Elements 1 and 2 are completely separate from each other, to be displaceable relative to one another without constraints. They are adapted to be arranged above the minor and major pectoralis muscles, 40 and 41. This embodiment is particularly suitable in cases where the natural breast has been removed entirely, e.g., due to cancer.

Figure 1B:
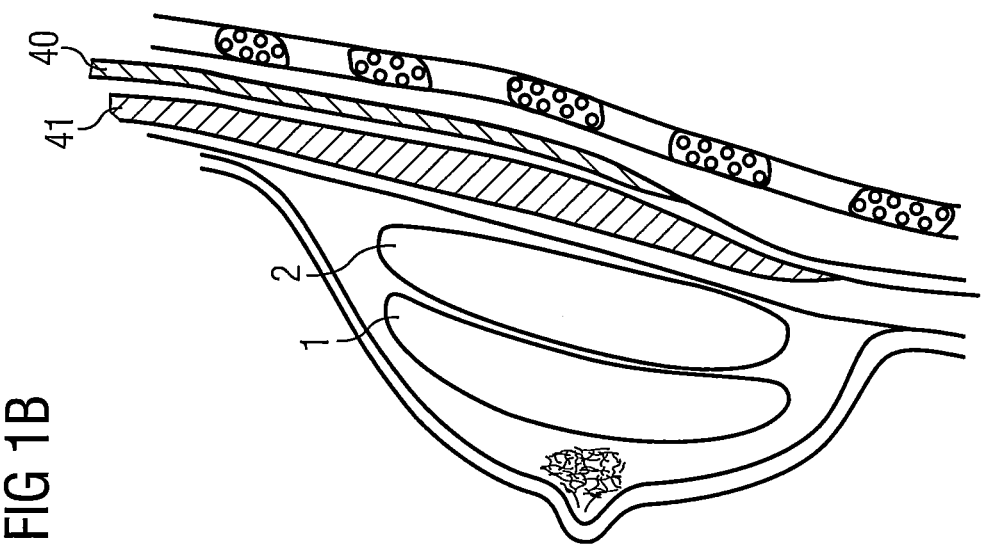

FIG. 1B shows the same elements 1 and 2 after manipulation from outside the breast. While the position of the second element 2 is substantially the same in both situations, the first element 1 has been displaced from a position partly below the second element 2 in FIG. 1A, to a position entirely on top of the second element 2 in FIG. 1B, so that the overall shape of the breast is changed from relatively flat in FIG. 1A, to relatively high in FIG. 1B.

Figure 2A:
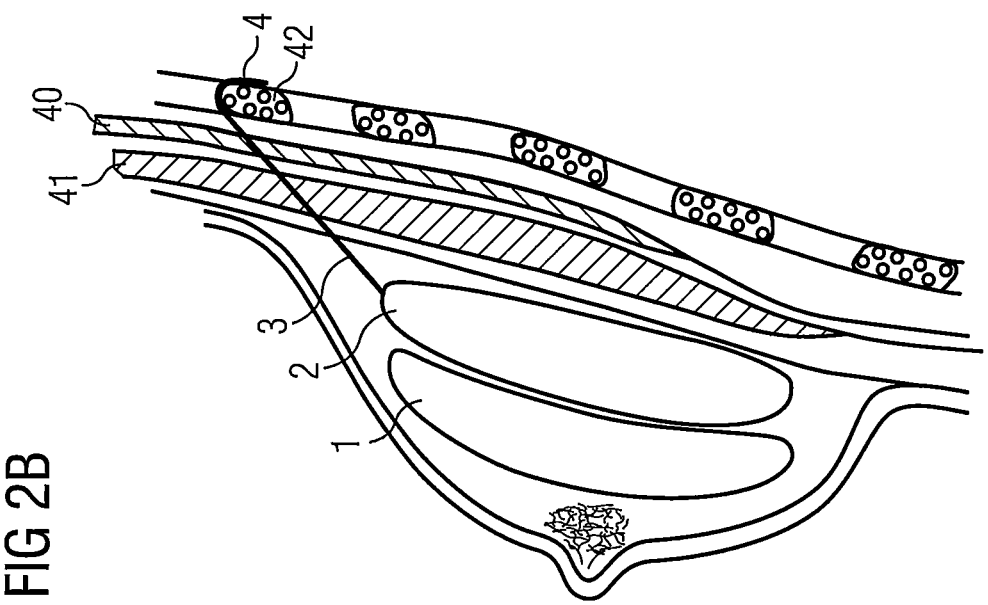
FIGS. 2A-2B show a breast implant system according to a second embodiment of the present invention.
Figure 2B:
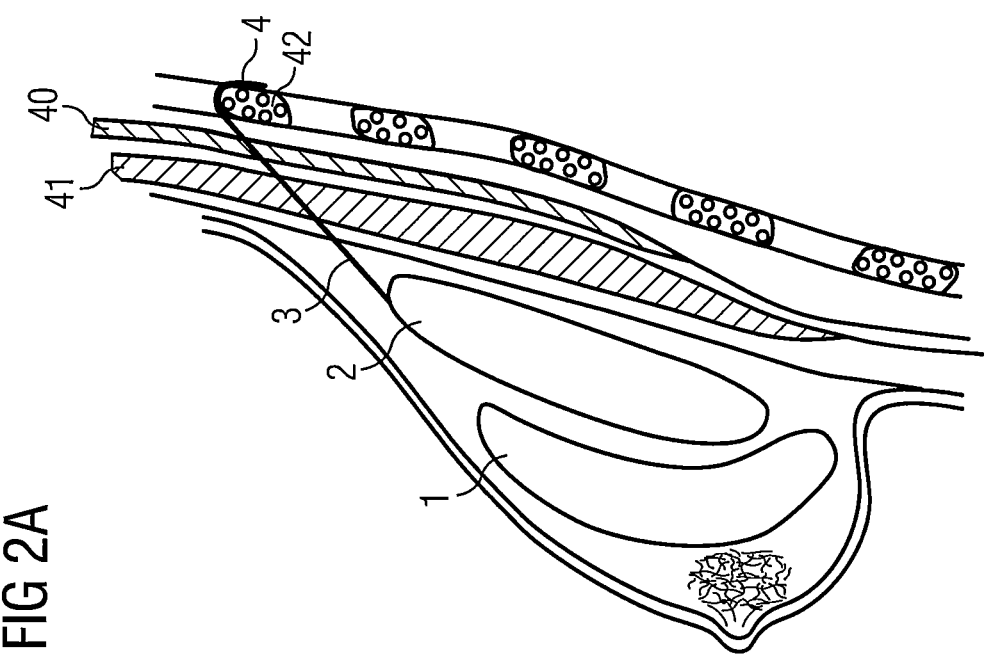

In order to ensure that the second element 2 remains substantially at the same position while the first element 1 is being displaced, the second element 2 may be fixedly mounted to the patient's bone structure. This is shown in FIGS. 2A and 2B, wherein a strap 3 is connected to the second element 2, and hinged to a substantially horizontal rib bone 42 via a hook 4. The hook 4 may be screwed to the bone. The representation in FIGS. 2A and 2B is to be understood merely as a principle.

FIGS. 3A and 3B show a third embodiment, differing from the previously described first and second embodiments in that the elements 1 and 2 are partly interconnected. For instance, elements 1 and 2 may be bonded together over a limited area, so that by manipulation from outside the breast the first element 1 can be "rolled" from the position shown in FIG. 3A, to on top of the second element 2, as shown in FIG. 3B.

The position of the second element 2 including the connecting area 5 remains unaffected.

Figure 3C:
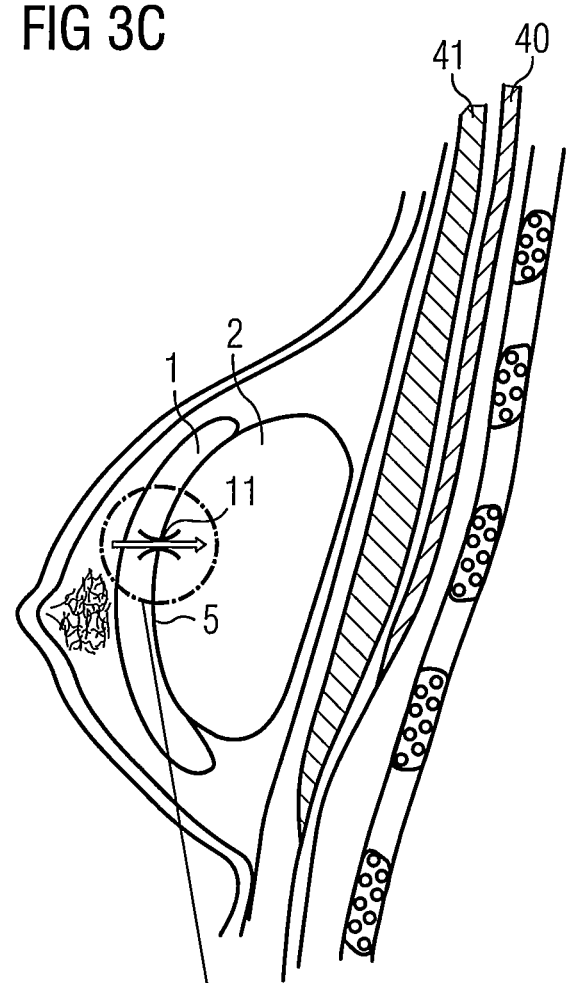

There may be provided one or more valves 11 in the connecting area 5 to allow content to be exchanged between the elements 1 and 2. These valves 11 are designed as pressure relief valves and can be of many different types. The purpose of the valves 11 is to allow fluid to flow from one element to the other element when a predetermined pressure difference is exceeded. In order to allow fluid to flow through the same valve in both directions, the valves 11 are formed as two-way pressure relief valves. A very simple way of providing such two-way pressure relief valve is shown in FIG. 3C. Here, a wall common to both elements 1 and 2 forms the connecting area 5. A slit 12 in the wall opens when a certain pressure difference between the adjacent elements is exceeded: The fluid exchange may further contribute to the shape change of the breast.

Figure 4A:
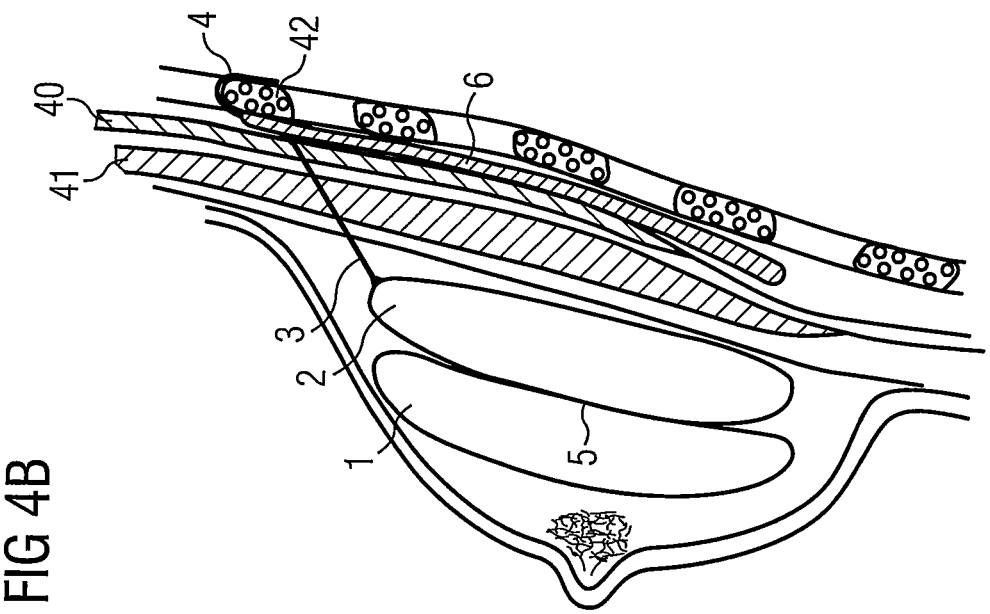
FIGS. 4A-4B show a breast implant system according to a fourth embodiment of the present invention.
Figure 4B:
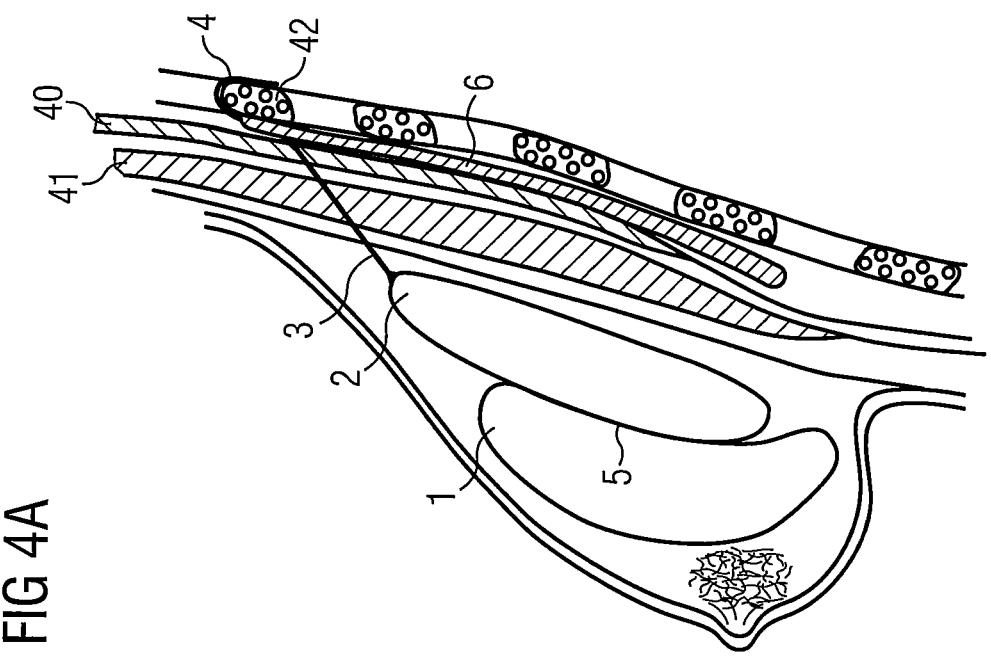

Due to the first and second elements 1 and 2 being interconnected, their relative movement is limited. This eases the process of reshaping the breast to the user. However, it is advantageous to fix the position of at least one of the elements in order to provide a basic structure. One possibility of fixedly mounting an element within the patient's body is shown in FIG. 4A. Accordingly, the second element 2, with the first element 1 attached thereto, is fixedly mounted to the patient's bone structure by means of a strap 3, similar to the second embodiment shown in FIGS. 2A and 2B. However, in the fourth embodiment, the strap 3 is not directly connected to the hinge 4, which is hinged over the rib bone, but via an intermediate plate 6 arranged between the rib 42 and the pectoralis muscles 40 and 41. The intermediate plate 6 may further be used for fixedly mounting further elements, or for mounting the second element 2 by means of more than only one strap 3, to define limits within which the second element 2 can be displaced.

FIGS. 5A to 5F show a fifth embodiment, which substantially differs from the previously described embodiments because the elements are contained in a casing for implantation, rather than being implanted separately. The casing consists of a back plate 12, and an outer flexible wall 13. The back plate 12 is preferably rigid and has a contour adapted to be placed adjacent the patient's thorax. The outer wall 13 is at least flexible, and may further be elastic to conform to any shape changes, including volume changes, in case that fluid can be supplied to, or withdrawn from, the interior of the elements. More preferably, the outer wall 13 may be filled with a liquid or gel type silicone, or with foam, or a combination thereof. In addition, bubbles of air or collagen may be incorporated in the silicone, foam, or other soft material. The compartment forming the outer wall 13 is completely separate from the internal elements. It can level out irregularities of the breast implant's outer shape and, more importantly, forms a barrier between the elements 1 contained in the casing and any fibroses that might form on the outside of the breast implant 10, and, further, forms a barrier for the lubricating fluid introduced into the casing from a reservoir R through connecting line 14.

The elements contained in the casing 12 and 13 can be rearranged within the casing to impart a certain shape on the breast implant 10. In this particular embodiment, a first element 1 and a second element 2 are contained in the casing 12 and 13. The first element 1 and the second element 2 have the form of a cushion or pad. As will be described below in relation to FIGS. 5E and 5F, elements 1 and 2 form fluid chambers with a variable fluid content. However, it is likewise possible that elements 1 and 2 rather have a constant volume and, e.g., are filled with granular material or a gel material. In the embodiment shown in FIGS. 5A to 5D, the second element 2 is fixedly mounted to the casing, more exactly to the rigid back plate 12, and the first element 1 is to a great extent freely movable within the casing 12, 13.

The breast implant system here includes a servo system for supplying lubricating fluid from the lubricating fluid reservoir into the casing 12 and 13. The lubricating fluid reservoir here consists of three sub-chambers R', R", and R"', of which only the first sub-chamber R' is in fluid connection with the interior of the casing 12 and 13 via fluid line 14. The entire servo system is implanted in the patient's body remotely from the breast implant 10. The first sub-chamber R' has the form of a bellows. The second sub-chamber R" cooperates with the first sub-chamber R', such that filling of the second sub-chamber R" with a fluid from the third sub-chamber R"' will cause the first sub-chamber R' to expand, and vice versa. Thus, when fluid is removed from the second sub-chamber R"

into the third sub-chamber R''', the length, and, thus, the volume of the first sub-chamber R' decreases. The situation is such, however, that the volume change in the second sub-chamber R'', which is also in the form of a bellows (see FIG. 5B), is less than the volume change in the first sub-chamber R'.

The way of supplying lubricating fluid from the first sub-chamber R' into the casing 12 and 13 will now be explained in relation to FIGS. 5A and 5B. That is, the patient has a subcutaneously arranged pressure chamber 23, in order to open a valve 24 arranged between the second and third sub-chambers R'' and R''' of the lubricating fluid reservoir, thereby allowing fluid to flow between the sub-chambers R'' and R'''. A preloaded spring 25 will cause the first sub-chamber R' to decrease, thereby urging not only fluid from the second sub-chamber R'' to flow to the third sub-chamber R''', but also lubricating fluid from the first sub-chamber R' to flow into the interior of the casing 12 and 13 of the breast implant 10. The resulting state of the breast implant system is shown in FIG. 5B.

Figure 5A:
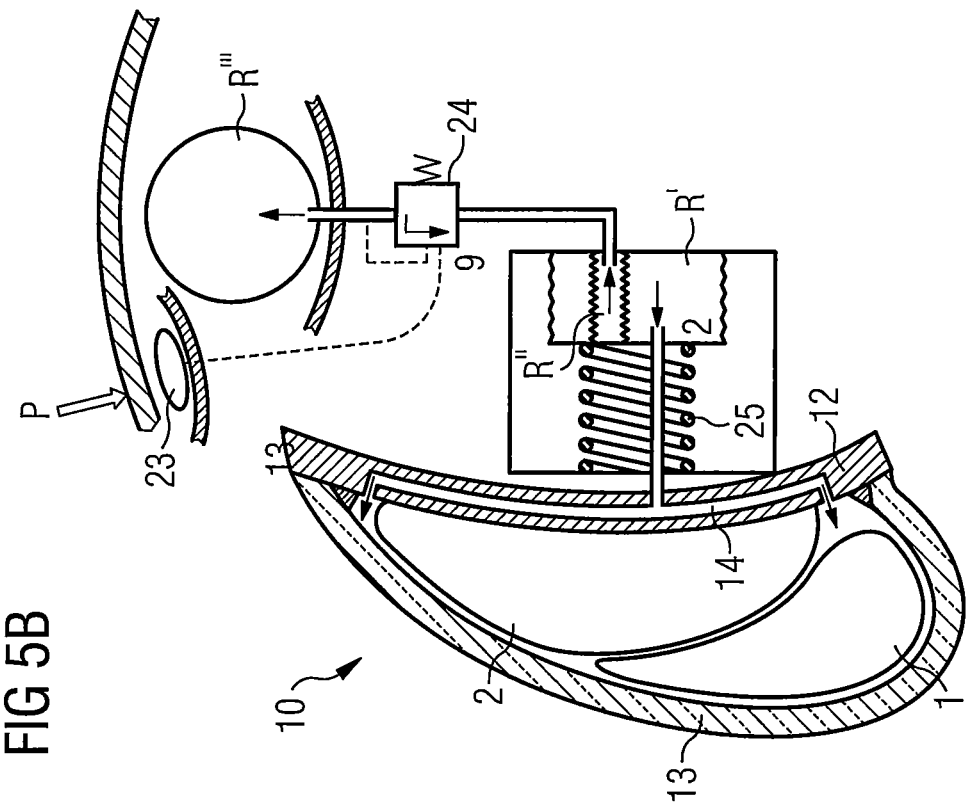
FIGS. 5A-5F show a breast implant system according to a fifth embodiment of the present invention.
Figure 5B:
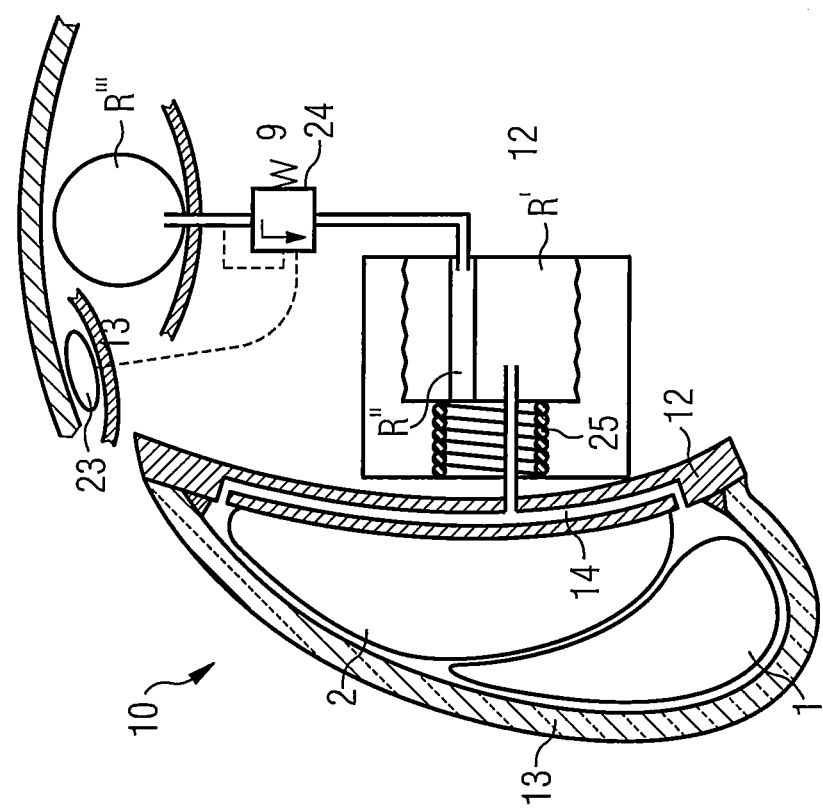
Figure 5C:
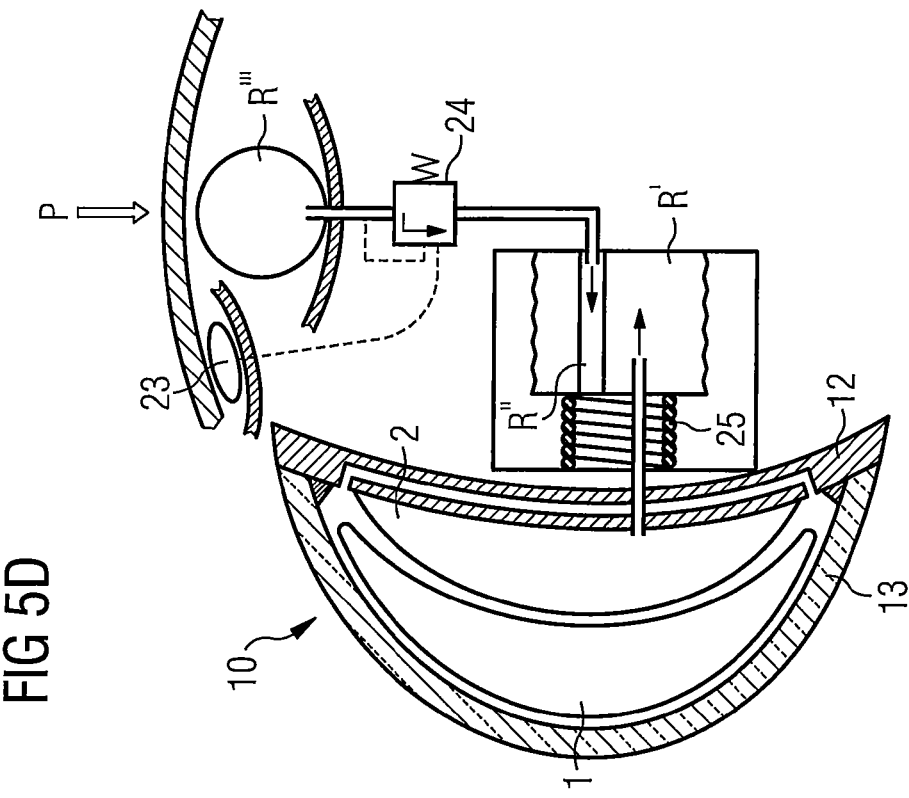
Figure 5D:
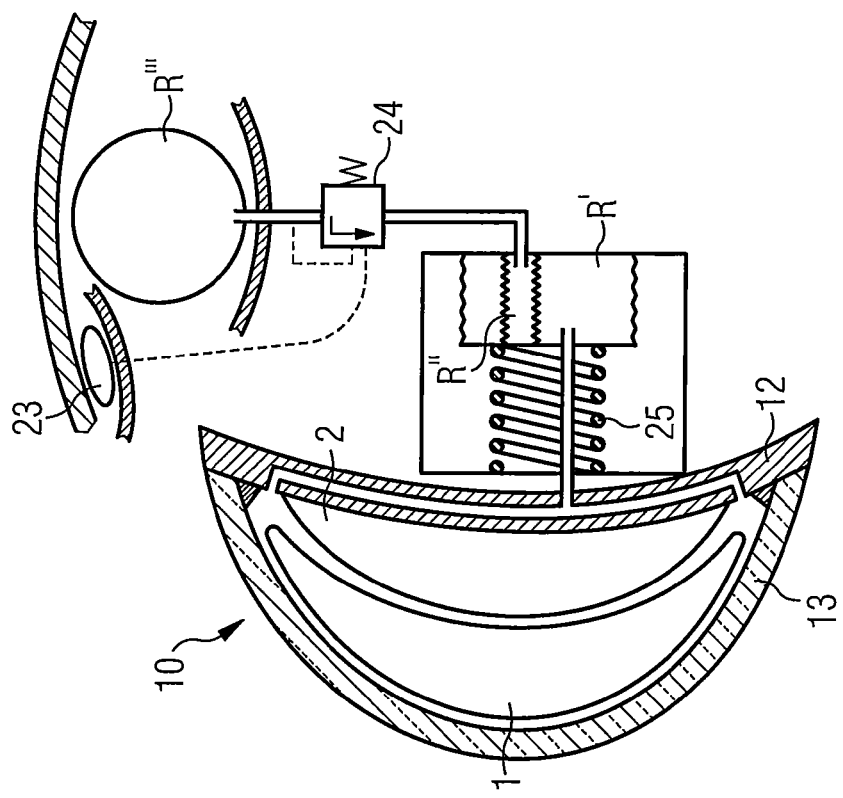

In this situation, the freely movable first element 1 can be displaced from a spot beside or, in the perspective shown, partly underneath the second element 2 to a different spot, such as on top of the second element 2 as shown in FIG. 5C, so as to change the outer shape of the breast implant 10 from relatively flat to relatively high. Once the relocation of the first element 1 has resulted in an appropriate shape change of the breast implant 10, the lubricating fluid has to be removed from the casing 12 and 13 again. Accordingly, the patient can simply compress the subcutaneously implanted third sub-chamber R''' of the lubricating fluid reservoir, as is indicated in FIG. 5D by arrow P. The increased pressure in the third sub-chamber R''' will cause the valve 24, which is designed as a pressure relief valve, to open so that fluid flows from the third sub-chamber R''' into the second sub-chamber R''. The second sub-chamber R'' will expand accordingly against the force of the spring 25 and, thus, compress the spring 25 so that it assumes again its initial position as in FIG. 5A. This will in turn cause the first sub-chamber R' to expand also, and the lubricating fluid will be drawn from the casing 12 and 13 of the breast implant 10 back into the remotely implanted first sub-chamber R' of the servo system. The subcutaneously implanted third sub-chamber R''' thus functions as a manually operable pump.

With the servo system shown in FIGS. 5A to 5D, the subcutaneously implanted third sub-chamber R''' can be kept relatively small so that it will not disturb the patient's appearance too much. For instance, it can advantageously be placed under the patient's arm. As a negative side effect, the pressure that the patient has to apply to the third sub-chamber R''' in order to overcome the force of the spring 25 is relatively high. However, if the spring load is kept small, this has the effect that the supply of lubricating fluid into the casing 12 and 13 of the breast implant 10 by automatic action of the spring 25 takes somewhat longer.

It should be noted that subcutaneously implanted pressure chamber 23 for actuation of valve 24 could be replaced with automatic components such as a switch and an electric motor. Likewise, instead of manually compressing the third sub-chamber R''', a pump and a motor driving the pump may be used, possibly activated by means of a subcutaneously implanted pressure switch.

Figure 5E:
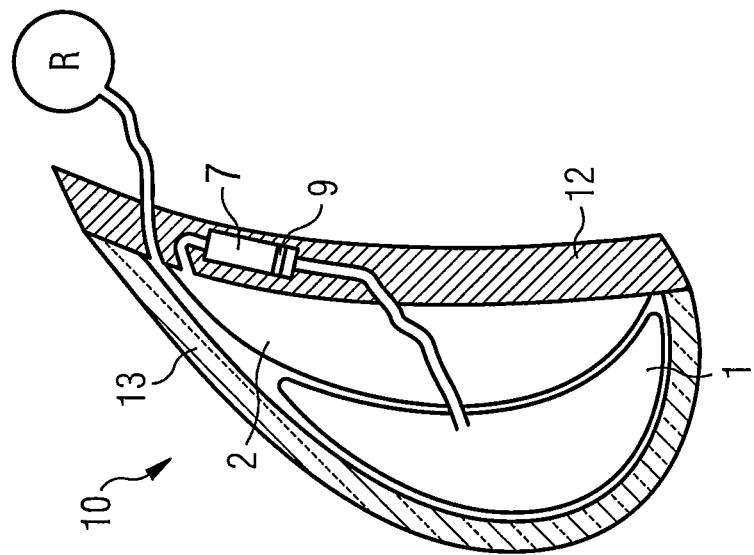
Figure 5F:
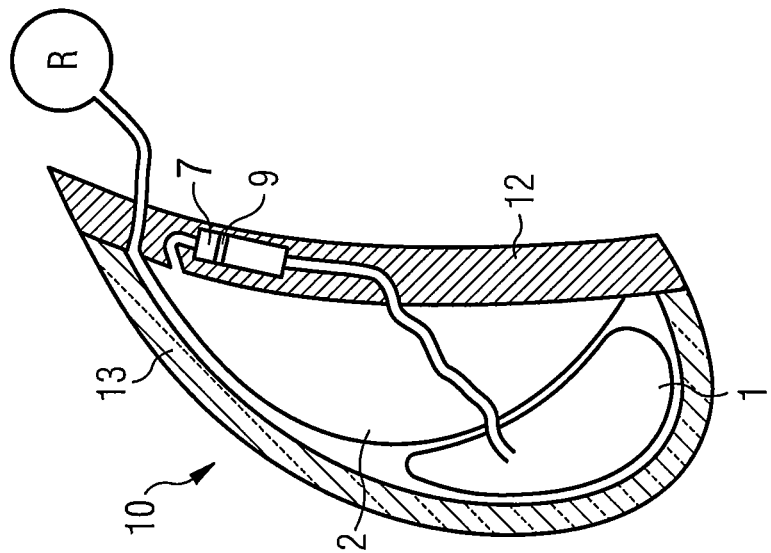

In addition to the lubricating fluid reservoir R (possibly even without a servo system, i.e. not separated in sub-chambers R' to R'''), the breast implant system may comprise a further reservoir, and/or pump, connected to the first and second elements 1 and 2 in order to remove fluid from one element, and supply an equivalent amount of fluid to the respective other element. This is shown in FIGS. 5E and 5F, which may be understood as showing a different cross section of the breast implant 10 of FIGS. 5A to 5D, without the lubricating fluid reservoir and its associated servo system. Thus, to change the shape of the breast implant, in addition to relocating the first element 1 within the casing 12 and 13 (or possibly more than only one such element), the shape can further be changed by inter-exchanging fluid between the elements 1 and 2. A fluid line 8 connects the interior of the first and second elements 1, 2 and runs, in the embodiments shown, through the rigid back plate 12. A pump, generally designated with reference numeral 9, is formed as a movable piston within a cylinder-like intermediate or "further" reservoir 7. The pump 9 is shown very schematically. It can have many different forms and can be of any suitable type. Instead of incorporating the pump in the rigid back wall 12, it may likewise be adapted for implantation remote from the breast implant 10, i.e. in an area with less space constraints. In addition, the actual manner of driving the pump, such as manually or automatically by means of a motor, is of no particular importance here and can be chosen appropriately. Using the moveable piston of the pump 9, fluid can be pumped and, thus, exchanged between the first and second elements 1 and 2. While the volume of the breast implant 10 remains unaffected by such fluid exchange, the combination of relocating elements within the casing 12 and 13, and inter-exchanging fluid among some or all of the elements 1 and 2 within the casing 12 and 13 offers a great variety of possibilities for adapting the shape of the breast implant 10. In any case, once the desired shape has been obtained, the lubricating fluid is withdrawn from the casing 3 and 4 back into the reservoir R.

Figure 3D:
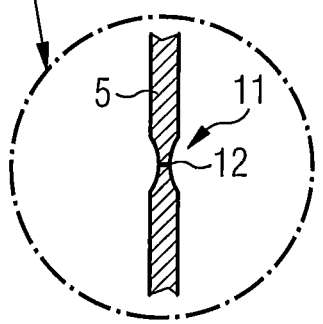

FIGS. 6A and 6B likewise show a breast implant 10 according to a sixth embodiment, with a first cushion-like or pad-like element 1 and a second cushion-like or pad-like element 2 accommodated in a casing 12 and 13, similar to FIGS. 5A and 5B. The lubricating fluid reservoir R connected to the interior of the casing 12 and 13 may or may not involve a servo system as explained in relation to FIGS. 5A to 5D. The difference, as compared to the embodiment shown in FIGS. 5E and 5F, lies in the fact that fluid cannot be inter-exchanged between the first and second elements 1 and 2, neither directly (such as described in relation to FIGS. 3C and 3D), nor via a pump (such as the pump 9 in FIGS. 5E, 5F). Rather, there is a separate fluid reservoir, $R_1$ and $R_2$, associated to each of the first and second elements 1 and 2. As can be seen from a comparison of FIGS. 5E and 5F with FIGS. 6A and 6B, the same shape change of the breast implant 10 from relatively flat to relatively high can be achieved. However, the embodiment shown in FIGS. 6A to 6B offers further options for changing not only the shape, but also the size of the breast implant 10, in that reservoirs $R_1$ and $R_2$ can be individually filled and emptied in order to individually deflate and inflate the associated first and second elements 1, 2.

Instead of being entirely freely movable within the casing 12 and 13, the first element 1 may be partly connected to the casing, e.g. to the wall 13, and/or to the second element 2, in order to limit the boundaries of movement thereof. For instance, elements 1 and 2 may be interconnected so that the fluid line from the first element 1 to the reservoir $R_1$ passes through the second element 2. Likewise, a valve such as the pressure relief valve 12 from FIGS. 3A and 3B may be present in the connecting area, or the connecting area may be completely closed. The connection may also comprise one or more straps by which the first element 1 is bound to neighboring surfaces.

FIGS. 7A to 7D show a seventh embodiment similar to the fifth embodiment, however, with the sole difference that the elements 1 contained in the casing 12 and 13 are not cushion-like or pad-like, but are much smaller, and may have the form of little balls. There may be hundreds of balls 1 contained in the casing 12 and 13, and these balls are preferably not fully inflated but have a slack wall so as to provide large contacting surfaces between adjacent balls 1. However, it is likewise possible that the elements 1 are made of fine granular and/or rigid material. In any case, it should be understood that FIGS. 7A and 7B only schematically show the principle that a great number of such elements 1 are contained in the casing 12 and 13. While FIGS. 7A to 7D show the elements as being spaced apart, they are, in fact, not spaced apart, but completely fill the interior of the casing 12 and 13, as their purpose is to define the outer shape of the overall breast implant 10.

Figure 7C:
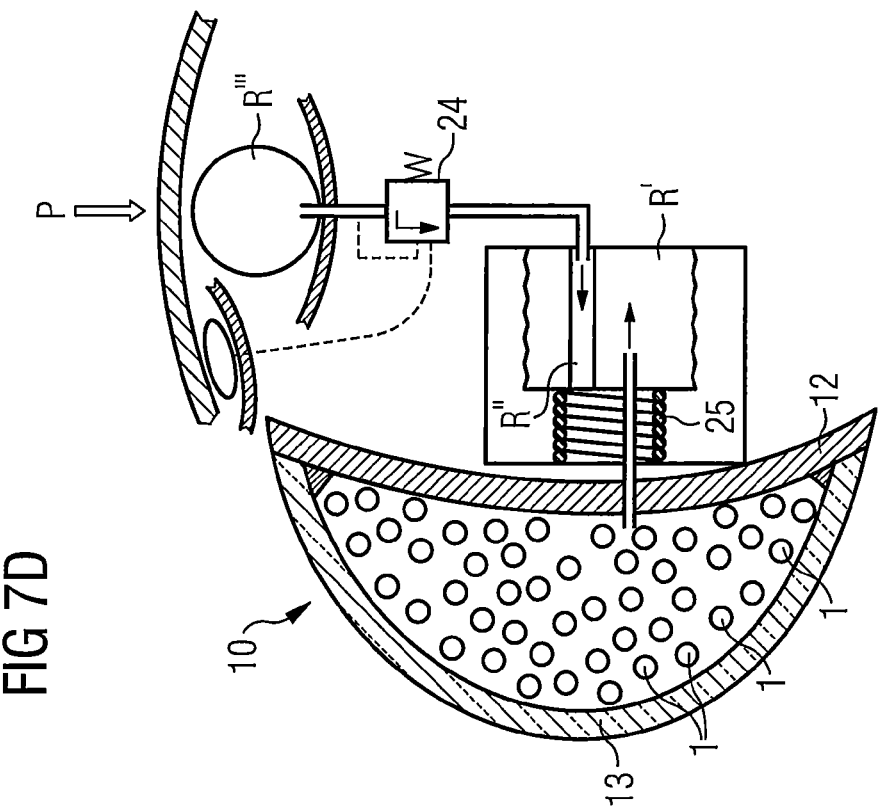
Figure 7D:
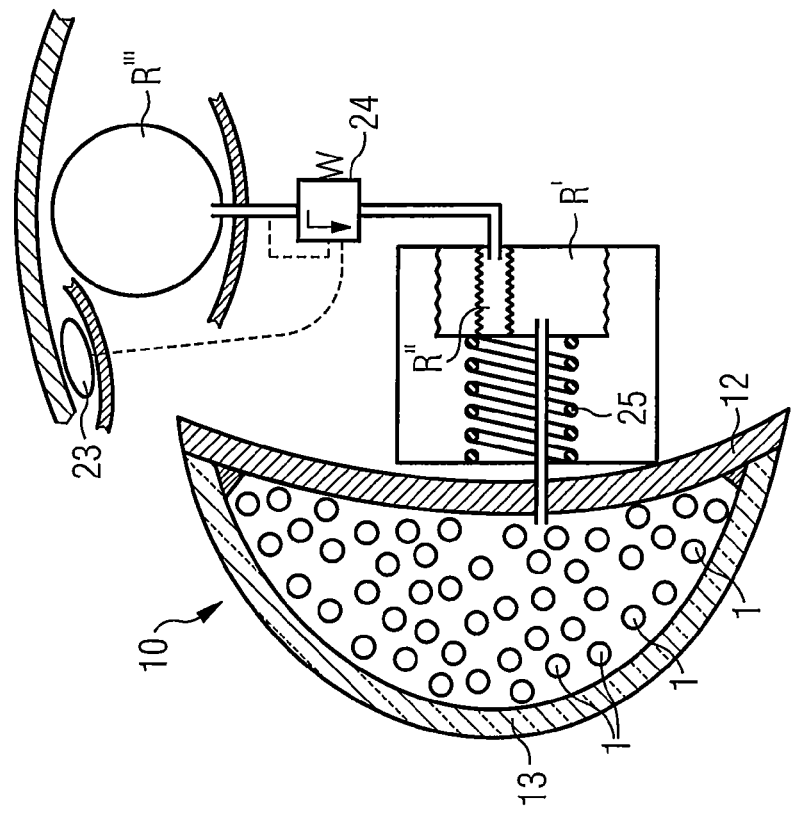

FIG. 7A shows an initial state in which the breast implant 10 is relatively flat, and the lubricating fluid is still contained in the first sub-chamber R' of the lubricating fluid reservoir. When a shape change is desired, lubricating fluid is first supplied from the first sub-chamber R' into the casing 12 and 13 using the servo system, as shown in FIG. 7B. Surface friction between the elements 1 contained in the casing 12 and 13 is accordingly reduced. This allows for manual manipulation of the breast implant 10 to achieve a different shape of the breast implant 10, which may be relatively high as shown in FIG. 7C. When satisfied with the achieved shape change, the lubricating fluid is withdrawn from the casing 12 and 13 by compressing the third sub-chamber R''' of the lubricating fluid reservoir, as indicated in FIG. 7D by arrow P. In the absence of the lubricating fluid, the surface friction among the elements 1 contained in the casing 12 and 13 substantially increases so that the change of the shape is maintained over long time.

A servo system similar to the one shown in FIGS. 7A to 7D may also be used in context with the fluid reservoirs $R_1$ and $R_2$ in FIGS. 6A and 6B, or any other reservoir for inflating and deflating one or more of the elements 1 and 2 contained in the casing 12 and 13.

In the eighth embodiment shown in FIGS. 8A and 8B, the lubricating fluid reservoir R is implanted subcutaneously. Furthermore, a plurality of medium-sized elements 1 is contained in the casing 12 and 13. FIG. 8A shows the system in a non-operated state. The reservoir R is fully expanded due to the force of a compressing spring 25 contained in the reservoir. Thus, the lubricating fluid reservoir R may be, e.g., of balloon-type or bellows-type. When a shape change is desired, the lubricating fluid reservoir R is compressed from outside the patient's body, as indicated in FIG. 8A by arrow P. The system with the reservoir R being compressed is not specifically shown in FIGS. 8A and 8B. However, once the lubricating fluid has been supplied from the reservoir R into the casing 12 and 13 by, e.g., the patient's left hand, surface friction between the elements 1 is accordingly reduced and the shape of the breast implant 10 can easily be manipulated manually using the right hand. Such manipulation will cause a relocation of the elements 1 between different spots within the casing 12 and 13, which in turn causes the outer shape of the breast implant 10 to change from relatively high in FIG. 8A to relatively flat in FIG. 8B, or vice versa. Once the desired shape is achieved, the pressure P on the reservoir R is released, and the elastic force of the spring 25 causes the lubricating fluid to be withdrawn from the casing 12 and 13 back into the reservoir R.

The elements 1 in the embodiment shown in FIGS. 8A and 8B are substantially smaller than the cushion-like elements, and are substantially larger than the ball-like elements in the previous embodiments. At least some of them may be interconnected so as to limit there relative movement, and/or at least some of them may be connected to the casing, so as to at least limit their movement in respect of the wall 13 or the back plate 12 of the casing 12 and 13. In addition, at least some of the elements 1 may be interconnected to allow for inter-exchanging fluid directly, or may be connected to one or more remotely implanted reservoirs via associated fluid conduits. Such fluid reservoirs may likewise be implanted subcutaneously for manual operation in the manner of a pump. All these options are not specifically shown in FIGS. 8A and 8B, and it is evident that these options are likewise applicable to the breast implant independent of the particular realization of the lubricating fluid reservoir R.

FIGS. 9A to 9B show a ninth embodiment, including a variation of how lubricating fluid can be supplied to, and removed from, the interior of the casing 12 and 13, which casing is displayed very schematically in FIGS. 9A and 9B. For reason of simplification, the elements filling the casing 12 and 13 are not shown in FIGS. 9A and 9B. The lubricating fluid reservoir R is again adapted for subcutaneous implantation here. First, pressure P is exerted on the reservoir R from outside the patient's body to urge fluid to flow through a two-way non-return valve 28, and through line 14 into the casing 12 and 13 (FIG. 9A). The two-way non-return valve 28 placed in line 14 connecting the reservoir R with the casing 12 and 13 is schematically shown in more detail in FIG. 9C. The form of the breast implant 10 can then be reshaped easily, e.g., by manual manipulation from outside the breast implant 10, or using automatic components, such as implanted elements including pump, motor, and the like. After reshaping is completed (FIG. 9B), pressure can be applied on the casing 12 and 13 from outside the breast implant 10 as uniformly as possible to avoid further rearrangement of the elements within the casing. Thus, upon manual compression of the breast implant 10, as indicated by arrows P in FIG. 9B, the lubricating fluid in the casing 12 and 13 is urged back through valve 28 into the remotely implanted reservoir R.

FIG. 10 shows a tenth embodiment of a more complex breast implant system. The basic structure of the breast implant system corresponds to the structure described above in relation to FIGS. 9A and 9B, but could also be completely different. What is important in the embodiment shown in FIG. 10 is a pump P driven by a motor M, and arranged to pump fluid between the reservoir R and the casing 12 and 13. The reservoir R may be implanted anywhere convenient in the patient's body, such as in the abdominal cavity.

The motor M is energized with wirelessly transmitted energy. For this purpose, the breast implant system comprises an energy transmitter 29 outside the patient's body, and an energy-transforming device 30 inside the patient's body, preferably subcutaneously implanted, to transform the wireless energy into electric energy. Though it is possible to make use of a motor M adapted to directly transform the wirelessly transmitted energy in kinetic energy, or, alternatively, to use the wirelessly transmitted energy transformed into electric energy, by means of the energy transforming device 30, to drive the motor M as the energy transforming device transforms the wireless energy into the electric energy, the specific embodiment shown in FIG. 10 first stores the transformed electric energy in an energy storage means E, before it is supplied to the motor M. Of course, it is also possible that a part of the transformed electric energy is directly used by the motor, while another part of the transformed electric energy is stored in the energy storage means E. The energy storage means E may include at least one accumulator, such as a rechargeable battery, and/or a capacitor. It is less convenient, but possible, to implant a regular battery as the energy storage means E. However, a regular battery may be used as the energy source to provide the wireless energy to be transmitted from outside the patient's body.

The breast implant system shown in the specific embodiment of FIG. 10 further includes a control unit. The control unit here comprises a first part C1, to be used by the patient from outside the patient's body, and a second part C2, to be implanted inside the patient's body. Data can thus be transmitted wirelessly between the first and second parts, C1 and C2, of the control unit. In addition or alternatively, the implantable second part C2 of the control unit may be programmable via the first part of the control unit. Preferably, the data are transmitted between the first and second parts, C1 and C2, of the control unit in the same manner as energy is transmitted, such as via the elements 29 and 30.

The external part C1 of the control unit may also be replaced with a simple manually operable switch for activating the implantable control unit C2. Such switch is then arranged for subcutaneous implantation to be operable from outside the patient's body. It is also possible to combine the switch with an external part C1 of the control unit.

Furthermore, feedback information may be sent between the implanted part C2 and the external part C1 of the control unit. Such feedback information may include information related to the energy to be stored in the energy storage means E. The control unit can make use of such feedback information for adjusting the amount of wireless energy transmitted by the energy transmitter 29. The feedback information may be related to an energy balance, which may be defined either: as the balance between an amount of wireless energy received inside the human body and an amount of energy consumed by the motor and pump; or, as the balance between a rate of wireless energy received inside the human body and a rate of energy consumed by the motor and pump.

FIG. 10 further shows an injection port 31 implanted under the patient's skin. Fluid can be added to or removed from the breast implant system through the injection port 31 by means of a regular syringe if need arises.

Clearly, a system like the one described in relation to FIG. 10 can also be used to inflate and deflate one or more of the elements (not shown) contained in the casing 12 and 13.

In context with an eleventh embodiment of a breast implant system, FIGS. 11A to 11D show a manner of implanting the lubricating fluid reservoir R remotely from the breast implant, next to the thorax under the pectoralis muscle. The casing of the breast implant 10 is here formed solely from the flexible wall 13, within which a great number of elements is contained, such as the previously described small balls. However, the breast implant 10 may also take any other form and configuration. It is designed to increase the volume of a natural breast 50, but can likewise be designed to replace an amputated breast. A pump 9 is also implanted remotely from the breast implant 10 to exchange fluid between the casing and the reservoir R. The pump 9 may be combined with a motor, control unit, and other parts of the system previously described. Instead of, or in addition to, the pump 9, other elements of the breast implant systems described before may be combined with this eleventh embodiment, such as remotely implanted components for manual operation by the patient, pressure relief valves, and so forth.

Figure 11A:
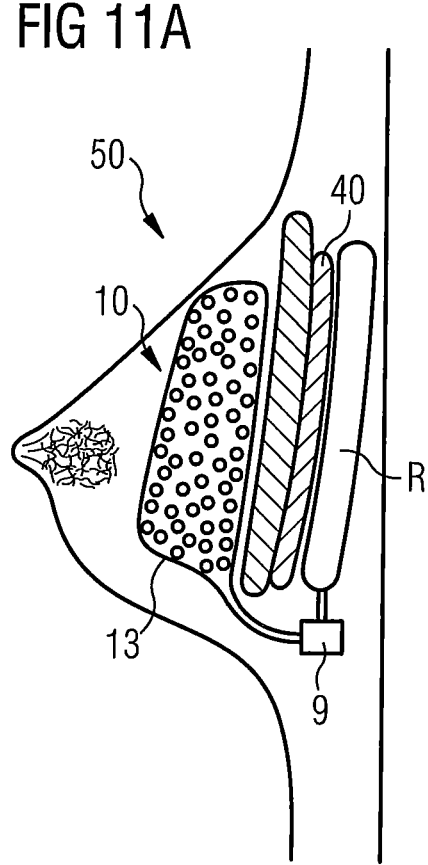
Figure 11B:
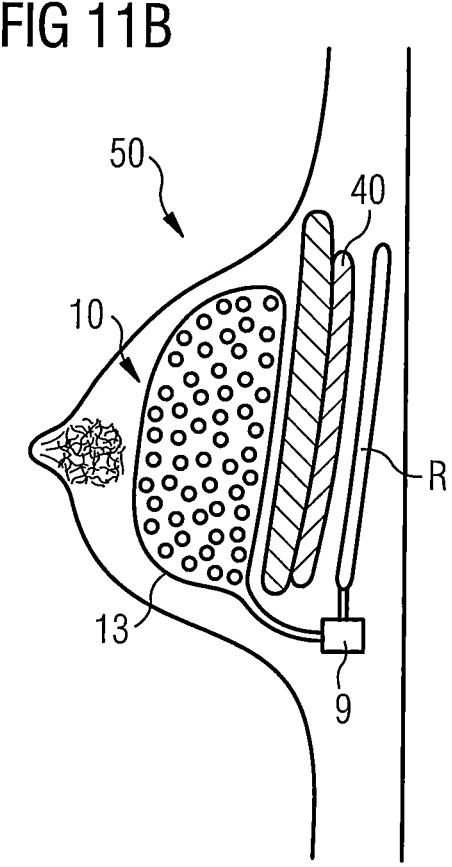

FIGS. 11A to 11D show the sequence of changing the shape of the breast implant 10. FIG. 11A shows an initial state with the breast 50 being neither flat nor high. FIG. 11B shows an intermediate state with the lubricating fluid from reservoir R being pumped into the casing using the pump 5. Surface friction among the elements contained in the casing is accordingly reduced, and permits easy reshaping of the breast implant 10 by manual manipulation. A possible result of the reshaping is shown in FIG. 11C. Once the desired shape has been achieved, pump 5 is used to withdraw the lubricating fluid from the casing back into the reservoir R, as shown in FIG. 11D. Surface friction among the elements contained in the casing is accordingly increased again to maintain the new shape of the breast implant 10.

Figure 12:
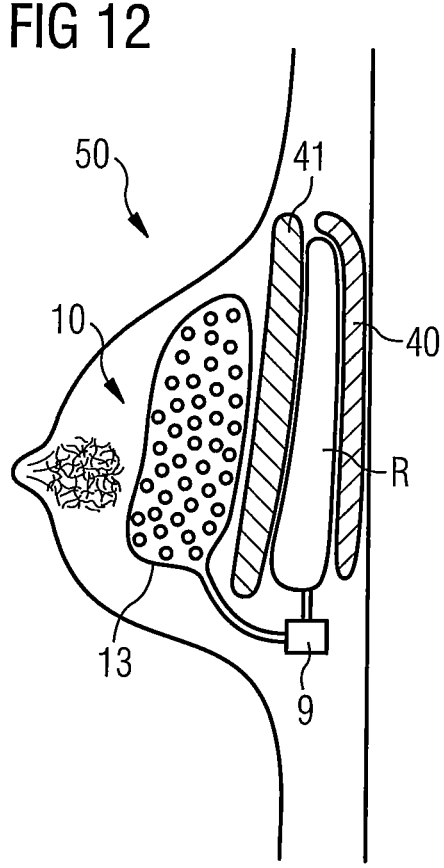
FIG. 12 shows a breast implant system according to a twelfth embodiment of the present invention.

Instead of implanting the reservoir R under the minor pectoralis muscle, it may likewise be placed between the patient's minor pectoralis muscle 40 and major pectoralis muscle 41, as is shown in FIG. 12. This arrangement may be more convenient for the patient.

It should be understood that, not only the lubricating fluid reservoir R, but also the further reservoir or reservoirs, if present, for changing the fluid content within one or more of the elements contained in the casing, can be placed under the minor pectoralis muscle, or between the minor and major pectoralis muscles, either along with the lubricating fluid reservoir R, or separate thereto.

The invention claimed is:

1. A breast implant system for implantation in a patient's body so as to form part of a breast implant, comprising at least one first element and at least one second element, each of the first and second elements comprising an outer wall defining a volume which is filled or fillable with a filling material, wherein the first element is displaceable relative to the second element by allowing the first element to be moved, when implanted in the patient's breast, between different spots within the patient's breast so as to change the outer shape of the breast implant, and wherein the breast implant system further comprises at least one reservoir in fluid connection with the at least one first element, such that fluid can be exchanged between the reservoir and the at least one first element.

2. The breast implant system of claim 1, comprising two or three or more of at least one of the first and second elements.

3. The breast implant system of claim 1, adapted to change the outer shape of the breast implant post-operatively.

4. The breast implant system of claim 3, adapted to change the outer shape of the breast implant non-invasively.

5. The breast implant system of claim 1, wherein the first and second elements are freely movable.

6. The breast implant system of claim 1, wherein the at least one first element is freely movable and the at least one second element is fixedly mounted.

7. The breast implant system of claim 1, wherein the first and second elements are interconnected so as to limit their relative displaceability.

8. The breast implant system of claim 1, wherein either or both of the first and second elements are mounted so as to be movable only between predetermined spots.

9. The breast implant system of claim 6, wherein the at least one first element is movable from a spot located at least partly beside the at least one second element, to a spot on top of the at least one second element, so as to change the outer shape of the breast implant from relatively flat to relatively high.

10. The breast implant system of claim 1, wherein the first and second elements form part of a common casing, the at least one first element being movable between different spots within the casing.

11. The breast implant system of claim 10, wherein the breast implant has a rigid back wall arranged to being placed adjacent the patient's thorax.

12. A breast implant system for implantation in a patient's body so as to form part of a breast implant, comprising at least one first element and at least one second element, each of the first and second elements comprising an outer wall defining a volume, wherein at least one of the first and second element is filled or fillable with a filling material, wherein the first element is displaceable relative to the second element by allowing the first element to be moved, when implanted in the patient's breast, between different spots within the patient's breast so as to change the outer shape of the breast implant, the breast implant system, further comprising a reservoir accommodating a lubricating fluid and connected to the casing, so as to allow lubricating fluid to be supplied to, and removed from, the casing in order to reduce surface friction between an outer surface of said at least one first element and surfaces contacting said outer surface.

13. The breast implant system of claim 10, comprising 10 or more of said first and second elements contained in the casing.

14. The breast implant system of claim 13, comprising 100 or more of said first and second elements contained in the casing.

15. The breast implant system of claim 10, wherein at least one of the outer wall of the first element and the outer wall of the casing is flexible.

16. The breast implant system of claim 10, wherein the outer wall of the casing has a shape adapted to allow lengthening of the functional length thereof without interfering with fibrosis covering said outer wall, when the breast implant is implanted in the body.

17. The breast implant system of claim 1, wherein the first and second elements each form a cushion containing the filling material and having a flexible outer wall.

18. The breast implant system of claim 1, wherein at least one first element and at least one second element are interconnected so as to allow for exchanging content between them.

19. The breast implant system of claim 18, wherein fluid can be exchanged between the first and second elements by manually compressing the one or the other, thereby urging fluid to flow from the one element into the other element.

20. A breast implant system for implantation in a patient's body so as to form part of a breast implant, comprising at least one first element and at least one second element, each of the first and second elements comprising an outer wall defining a volume, wherein at least one of the first and second element is filled or fillable with a filling material, wherein the first element is displaceable relative to the second element by allowing the first element to be moved, when implanted in the patient's breast, between different spots within the patient's breast so as to change the outer shape of the breast implant, the breast implant system, further comprising at least one reservoir in fluid connection with both at least one of the at least one first element and at least one of the at least one second element, such that fluid can be exchanged between the reservoir and said first and second elements, so as to change their respective content.

21. The breast implant system of claim 20, wherein the at least one reservoir is adapted for implantation below the minor pectoralis muscle, or between the major and the minor pectoralis muscles.

22. A breast implant system for implantation in a patient's body so as to form part of a breast implant, comprising at least one first element and at least one second element, each of the first and second elements comprising an outer wall defining a volume, wherein at least one of the first and second element is filled or fillable with a filling material, wherein the first element is displaceable relative to the second element by allowing the first element to be moved, when implanted in the patient's breast, between different spots within the patient's breast so as to change the outer shape of the breast implant, the breast implant system, further comprising at least one reservoir adapted for implantation within the patient's body remotely from the breast implant, the system further comprising at least one conduit between the at least one reservoir and one or more of the first and second elements for fluid exchange between the at least one reservoir and the one or more elements.

23. The breast implant system of claim 1, further comprising at least one pump.

24. A breast implant system for implantation in a patient's body so as to form part of a breast implant, comprising at least one first element and at least one second element, each of the first and second elements comprising an outer wall defining a volume, wherein at least one of the first and second element is filled or fillable with a filling material, wherein the first element is displaceable relative to the second element by allowing the first element to be moved, when implanted in the patient's breast, between different spots within the patient's breast so as to change the outer shape of the breast implant, the breast implant system, further comprising at least one pump and at least one motor arranged for automatically driving the pump.

25. A breast implant system for implantation in a patient's body so as to form part of a breast implant, comprising at least one first element and at least one second element, each of the first and second elements comprising an outer wall defining a volume, wherein at least one of the first and second element is filled or finable with a filling material, wherein the first element is displaceable relative to the second element by allowing the first element to be moved, when implanted in the patient's breast, between different spots within the patient's breast so as to change the outer shape of the breast implant, the breast implant system, further comprising at least one pump and a control unit adapted to directly or indirectly control the at least one pump or another component of the system.

26. The breast implant system of claim 1, wherein the at least one reservoir is adapted for implantation below the minor pectoralis muscle, or between the major and the minor pectoralis muscles.

27. The breast implant system of claim 12, wherein the at least one reservoir is adapted for implantation below the minor pectoralis muscle, or between the major and the minor pectoralis muscles.

28. The breast implant system of claim 22, wherein the at least one reservoir is adapted for implantation below the minor pectoralis muscle, or between the major and the minor pectoralis muscles.

29. The breast implant system of claim 25, comprising at least one reservoir adapted for implantation below the minor pectoralis muscle, or between the major and the minor pectoralis muscles.

30. The breast implant system of claim 12, further comprising at least one pump.

31. The breast implant system of claim 20, further comprising at least one pump.

32. The breast implant system of claim 22, further comprising at least one pump.

33. The breast implant system of claim 12, wherein at least one first element and at least one second element are interconnected so as to allow for exchanging content between them.

34. The breast implant system of claim 33, wherein fluid can be exchanged between the at least one first and second elements by manually compressing the one or the other, thereby urging fluid to flow from the one element into the other element.

35. The breast implant system of claim 20, wherein at least one first element and at least one second element are interconnected so as to allow for exchanging content between them.

36. The breast implant system of claim 35, wherein fluid can be exchanged between the first and second elements by manually compressing the one or the other, thereby urging fluid to flow from the one element into the other element.

37. The breast implant system of claim 22, wherein at least one first element and at least one second element are interconnected so as to allow for exchanging content between them.

38. The breast implant system of claim 37, wherein fluid can be exchanged between the at least one first and second elements by manually compressing the one or the other, thereby urging fluid to flow from the one element into the other element.

39. The breast implant system of claim 25, wherein at least one first element and at least one second element are interconnected so as to allow for exchanging content between them.

40. The breast implant system of claim 1, wherein the filling material of at least one of the first and the second elements is in granular form.

41. The breast implant system of claim 20, wherein the filling material of at least one of the first and the second elements is in granular form.

42. The breast implant system of claim 22, wherein the filling material of at least one of the first and the second elements is in granular form.

43. The breast implant system of claim 12, wherein the system is adapted to change the outer shape of the breast implant post-operatively and non-invasively.

44. The breast implant system of claim 12, further comprising 10 or more of the at least one first and second elements contained in the casing.

45. The breast implant system of claim 12, wherein the outer wall of the casing has a shape adapted to allow lengthening of the functional length thereof without interfering with fibrosis covering said outer wall, when the breast implant is implanted in the body.

46. The breast implant system of claim 20, wherein the system is adapted to change the outer shape of the breast implant post-operatively and non-invasively.

47. The breast implant system of claim 20, further comprising 10 or more of the at least one first and second elements contained in the casing.

48. The breast implant system of claim 20, wherein the outer wall of the casing has a shape adapted to allow lengthening of the functional length thereof without interfering with fibrosis covering said outer wall, when the breast implant is implanted in the body.

49. The breast implant system of claim 22, wherein the system is adapted to change the outer shape of the breast implant post-operatively and non-invasively.

50. The breast implant system of claim 22, further comprising 10 or more of the at least one first and second elements contained in the casing.

51. The breast implant system of claim 22, wherein the outer wall of the casing has a shape adapted to allow lengthening of the functional length thereof without interfering with fibrosis covering said outer wall, when the breast implant is implanted in the body.

52. The breast implant system of claim 25, wherein the system is adapted to change the outer shape of the breast implant post-operatively and non-invasively.

53. The breast implant system of claim 25, further comprising 10 or more of the at least one first and second elements contained in the casing.

54. The breast implant system of claim 25, wherein the outer wall of the casing has a shape adapted to allow lengthening of the functional length thereof without interfering with fibrosis covering said outer wall, when the breast implant is implanted in the body.

* * * * *